(12) United States Patent
Venkatraman et al.

(10) Patent No.: US 8,933,058 B2
(45) Date of Patent: Jan. 13, 2015

(54) TARGETTED DRUG DELIVERY TO THE BONE

(75) Inventors: Subramanian Venkatraman, Singapore (SG); Say Chye Joachim Loo, Singapore (SG)

(73) Assignee: Nanyang Technological University, Singapore (SG)

( * ) Notice: Subject to any disclaimer, the term of this patent is extended or adjusted under 35 U.S.C. 154(b) by 0 days.

(21) Appl. No.: 13/375,713

(22) PCT Filed: Jun. 7, 2010

(86) PCT No.: PCT/SG2010/000214
§ 371 (c)(1),
(2), (4) Date: Feb. 22, 2012

(87) PCT Pub. No.: WO2010/140986
PCT Pub. Date: Dec. 9, 2010

(65) Prior Publication Data
US 2012/0142641 A1    Jun. 7, 2012

Related U.S. Application Data

(60) Provisional application No. 61/184,548, filed on Jun. 5, 2009.

(51) Int. Cl.
*A61K 31/663* (2006.01)
*A61P 19/08* (2006.01)
*C07F 9/38* (2006.01)
*A61K 47/48* (2006.01)

(52) U.S. Cl.
CPC ..... *A61K 47/48861* (2013.01); *A61K 47/48015* (2013.01); *C07B 2200/11* (2013.01); *C07F 9/3869* (2013.01); *C07F 9/386* (2013.01); *C07F 9/3873* (2013.01)
USPC .......................................... 514/107; 514/108

(58) Field of Classification Search
CPC .................. A61K 47/48015; A61K 47/48861; C07B 2200/11; C07F 9/386; C07F 9/3869; C07F 9/3873
USPC .................................................. 514/107, 108
See application file for complete search history.

(56) References Cited

U.S. PATENT DOCUMENTS

| | | | |
|---|---|---|---|
| 5,003,069 A | 3/1991 | McGill et al. | |
| 2003/0013686 A1* | 1/2003 | Golomb et al. | 514/102 |

FOREIGN PATENT DOCUMENTS

| | | | |
|---|---|---|---|
| EP | 0275215 B1 * | 1/1988 | |
| EP | 0 275 215 B1 | 7/1988 | |
| WO | WO 02/062398 A2 | 8/2002 | |
| WO | WO 02062398 A2 * | 8/2002 | |
| WO | WO 2008/098959 A1 | 8/2008 | |

OTHER PUBLICATIONS

Adzamli, I. K. et al., *Development of Phosphonate Derivatives of Gadolinium Chelates for NMR Imaging of Calcified Soft Tissues*, J. Med. Chem. 32 (1989) 139-144.

Bhadra, D. et al., *A PEGylated Dendritic Nanoparticulate Carrier of Fluorouracil*, International Journal of Pharmaceutics 257 (2003) 111-124.

Burgada, R. et al., *Synthèse de ligands bisphosphoniques pour la complexation de l'ion uranyle du cobalt et du fer*, C. R. Chimie 7 (2004) 35-39.

Chen, H. et al., *Cytotoxicity, Hemolysis, and Acute in Vivo Toxicity of Dendrimers Based on Melamine, Candidate Vehicles for Drug Delivery*, J. Am. Chem. Soc. 126 (2004) 10044-10048.

Grimsdale, A. C. et al., *The Chemistry of Organic Nanomaterials*, Angew. Chem Int. Ed. 44 (2005) 5592-5629.

Hortobagyi, G. N. et al., *Efficacy of Pamidronate in Reducing Skeletal Complications in Patients With Breast Cancer and Lytic Bone Metastases*, The New England Journal of Medicine, vol. 335, No. 24, (1996) 1785-1791.

Hynes, J. Jr. et al., *N-Amination of Pyrrole and Indole Heterocycles with Monochloramine ($NH_2Cl$)*, J. Org. Chem. 69 (2004) 1368-1371.

Jain, A. K. et al., *Skeletal Drug Delivery Systems*, International Journal of Pharmaceutics 206 (2000) 1-12.

Jongpaiboonkit, L. et al., *Mineral-Coated Polymer Microspheres for Controlled Protein Binding and Release*, Adv. Mater. 21 (2009) 1960-1963.

Krisanapiboon, A. et al., *Biocompatability of Hydroxyapatite Composite as a Local Drug Delivery System*, Journal of Orthopaedic Surgery 14 (3) (2006) 315-318.

Larsen, R. H. et al., $^{211}$*At- and* $^{131}$*-Labeled Bisphosphonates with High In Vivo Stability and Bone Accumulation*, The Journal of Nuclear Medicine, vol. 40, No. 7 (1999) 1197-1203.

Neves, M. et al., *Synthesis, Characterization and Biodistribution of Bisphosphonates Sm-153 Complexes: Correlation with Molecular Modeling Interaction Studies*, Nuclear Medicine and Biology 29 (2002) 329-338.

Ogawa, K. et al., *Therapeutic Effects of a* $^{186}$*Re-Complex-Conjugated Bisphosphonate for the Palliation of Metastatic Bone Pain in an Animal Model*, The Journal of Nuclear Medicine, vol. 48, No. 1 (2007) 122-127.

Rauschmann, M. A. et al., *Nanocrystalline Hydroxyapatite and Calcium Sulphate as Biodegradable Composite Carrier Material for Local Delivery of Antibiotics in Bone Infections*, Biomaterials 26 (2005) 2677-2684.

Shinto, Y. A. et al., *Calcium Hydroxyapatite Ceramic Used as a Delivery System for Antibiotics*, The Journal of Bone and Joint Surgery, vol. 74-B, No. 4 (1992) 600-604.

Sunder, M. et al., *Biphasic Calcium Phosphates for Antibiotic Release*, Trends Biomater. Artif. Organs, vol. 18(2) (2005) 213-218.

(Continued)

*Primary Examiner* — Janet Epps-Smith
*Assistant Examiner* — Courtney Brown
(74) *Attorney, Agent, or Firm* — Alston & Bird LLP

(57) ABSTRACT

The present invention relates to a complex of a bisphosphonate compound, methods of preparing such complex and uses thereof.

26 Claims, 10 Drawing Sheets

(56) References Cited

OTHER PUBLICATIONS

Tomalia, D. A. et al., *A New Class of Polymers: Starburst-Dendritic Macromolecules*, Polymer Journal, vol. 17, No. 1 (1985) 117-132.
Uludag, H., *Bisphosphonates as a Foundation of Drug Delivery to Bone*, Current Pharmaceutical Design 8 (2002) 1929-194.
Xu, O. et al., *Encapsulation and Release of a Hydrophobic Drug from Hydroxyapatite Coated Liposomes*, Biomaterials 28 (2007) 2687-2694.
Zhuo, R. X. et al., *In Vitro Release of 5-Fluorouracil With Cyclic Core Dendritic Polymer*, Journal of Controlled Release 57 (1999) 249-257.
*Managing Care—Should We Adopt a New Ethic?*, The New England Journal of Medicine, vol. 339, No. 6 (1998) 397-404.
Denissen, H., et al., "Degradable Bisphosphonate-Alkaline Phosphatase-Complexed Hydroxyapatite Implants In Vitro," *Journal of Bone and Mineral Research*, 1997, vol. 12(2), pp. 290-297.
Josse, S., et al., "Novel biomaterials for bisphosphonate delivery," *Biomaterials*, 2005, vol. 26, pp. 2073-2080.
Sawicki, et al., "Bisphosphonate sequestering agents, Synthesis and preliminary evaluation for in vitro and in vivo uranium (VI) chelation," *European Journal of Medicinal Chemistry*, 2008, vol. 43, pp. 2768-2777.

* cited by examiner

TARGETTED DRUG DELIVERY TO THE BONE

CROSS-REFERENCE TO RELATED APPLICATIONS

This application claims the benefit of priority of U.S. provisional application No. 61/184,548, filed Jun. 5, 2009, the content of which being hereby incorporated by reference in its entirety for all purposes.

FIELD OF THE INVENTION

The present invention relates to complexes of a bisphosphonate or a phosphonate compound, methods of preparing such complexes and uses thereof. The invention also relates to a method of treating or preventing bone-related diseases or disorders and a pharmaceutical composition of the respective complexes. The invention also relates to bisphosphonate compounds as such.

BACKGROUND OF THE INVENTION

Bisphosphonates are a class of drugs that have been used to treat bone-related diseases such as osteoporosis and other disorders such as associated loss of bone mass and strength. Bisphosphonates prevent the resorption of bone, thereby reducing occurrences of fractures in the spine or hip for example. Bisphosphonates are chemical analogues of pyrophosphate where the central P—O—P linkage has been replaced by the P—C—P bond. The diphosphonate group imparts sufficient affinity to the mineral phase of the bone so that administration of bisphosphonates results in a significant amount of deposition to the osseous tissue of the bone. Many bisphosphonate analogues are currently available for enhancing bone affinity and improving pharmacological activity. Besides their primary use in treating metabolic bone disease osteoporosis and Paget's disease, recent studies have shown that bisphosphonates can be used in tumours affecting the skeleton. It has been reported in New England Journal of Medicine, 335: 1785-1791 (1996) that treatment with bisphosphonates decreases the frequency of skeletal events for patients with multiple myeloma involving bone and breast cancer with osteolytic metastases. Furthermore, adjunctive treatment with bisphosphonates was shown to reduce the incidence and number of new bone and visceral metastases in women with high risk, breast cancer (New England Journal of Medicine, 339:398-400 (1998). However, there remains a need for new approaches that would improve drug efficacy and reduce the associated side effects.

Another example of a bone-related disease that is potentially a major orthopaedic problem is chronic osteomyelitis. Chronic osteomyelitis is caused by microorganisms infecting the bone and/or the bone marrow. The infection associated with osteomyelitis may be localized or it may spread through the periosteum, cortex, marrow, and cancellous tissue. Osteomyelitis can be treated medically or surgically and prolonged antibiotic therapy is normally used. However, there are serious side effects such as nephrotoxicity and hepatotoxicity associated with such treatment. Several delivery systems and materials have been used in order to provide efficient antibiotic delivery. Materials such as polymethylmathacrylate (PMMA) and other biodegradable materials such as hydroxyapatite, plaster of Paris and chitosan were used. A porous calcium hydroxyapatite ceramic (CHA) was used for sustained release of antibiotics by incorporating the antibiotics into the CHA blocks. (Shinto Y. et al, *The Journal of Bone and Joint Surgery,* 1992, 74-B: 600-604). PMMA loaded with a variety of antibiotics have been extensively studied (Jain A K et al, Skeletal Drug Delivery Systems, *Int. J. Pharm,* 2000, 206:1-12). A hydroxyapatite composite comprising plaster of Paris, chitosan and hydroxyapatite impregnated with an antibiotic was also studied (Krisanapiboon A. et al, *Journal of Orthopaedic Surgery,* 2006, 14(3): 315-318). However a major drawback encountered with the treatment of osteomyelitis is the risk of antibiotic resistance.

Thus, there is a need to provide a new way for targeting drug delivery to the bone. This need is solved by the complex and the respective uses of the complex including its pharmaceutical uses.

SUMMARY OF THE INVENTION

In one aspect the invention provides a complex of formula (I) of a bisphosphonate compound of formula (II), the complex adapted to target a bone,

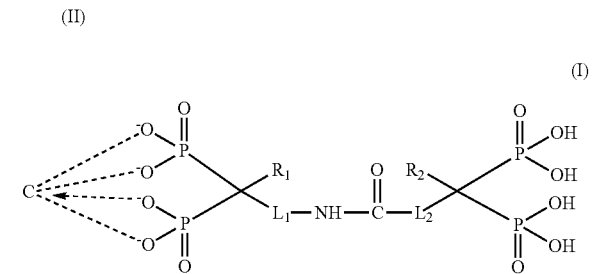

wherein, in formula (I), C represents a carrier to which the bisphosphonate compound of formula (II) is bound thereto, and wherein in formula (II), $R_1$ and $R_2$ are each independently selected from the group consisting of hydrogen, halogen, hydroxyl, optionally substituted $C_1$-$C_{10}$ alkyl, optionally substituted $C_2$-$C_6$ alkenyl, optionally substituted $C_2$-$C_6$ alkynyl, optionally substituted $C_1$-$C_6$ acyl, optionally substituted $C_{3-8}$ cycloalkyl, and optionally substituted $C_{3-8}$ cycloalkenyl; and $L_1$ and $L_2$ are each a linker having a main chain comprising 0 to 20 main chain atoms.

In another aspect, the invention provides a pharmaceutical composition. The pharmaceutical composition includes the complex as defined above and a pharmaceutically acceptable carrier or excipient.

In a further aspect, the invention provides a method for the treatment or prevention of a bone-related disease or disorder. The method includes administering a pharmaceutically active amount of a complex as defined above to a subject in need thereof.

In yet another aspect, the invention provides a complex as defined above for use in the treatment or prevention of a bone-related disease or disorder.

In yet a further aspect, the invention provides a method of preparing the complex of formula (I). The method includes reacting a compound of formula (IIa)

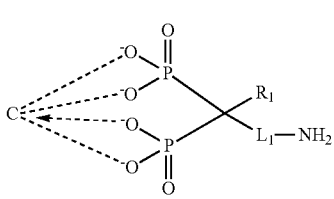

(IIa)

with a compound of formula (III),

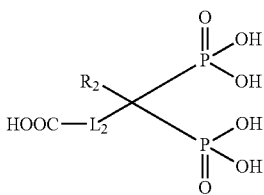

(III)

under conditions to form the complex of formula (I).

In another aspect, the invention provides a compound of formula (II)

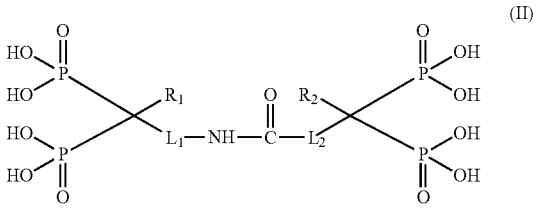

(II)

wherein
$R_1$ and $R_2$ are each independently selected from the group consisting of hydrogen, halogen, hydroxyl, optionally substituted $C_1$-$C_{10}$ alkyl, optionally substituted $C_2$-$C_6$ alkenyl, optionally substituted $C_2$-$C_6$ alkynyl, optionally substituted $C_1$-$C_6$ acyl, optionally substituted $C_{3-8}$ cycloalkyl, and optionally substituted $C_{3-8}$ cycloalkenyl; and $L_1$ and $L_2$ are each a linker having a main chain comprising 0 to 20 main chain atoms.

In yet another aspect, the invention provides a complex of formula (VI)

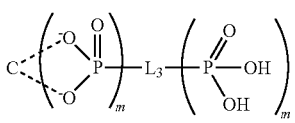

(VI)

In formula (VI), C represents a carrier to which the phosphonate compound is bound thereto,
$L_3$ is a linker having a main chain comprising 1 to 20 main chain atoms; and
m is an integer of 1 to 10.

DETAILED DESCRIPTION OF THE INVENTION

In the complexes of formula (I) or formula (VI), the respective bisphosphonate compound or phosphonate compound can be bound to the carrier (C) via any non-covalent bonds, as long as a stable complex of formula (I) or (VI) is formed. Such non-covalent bonding can, for example, include hydrogen bonds or ionic interactions between the carrier and the respective diphosphonate groups of the compound of formula (II) or the phosphonate groups of the complex of formula (VI). In some embodiments, the hydroxyl ions of the bisphosphonate compound of formula (II) can form ionic interactions with a metal ion of the carrier, for example $Ca^{2+}$ ions. The interaction can also occur via chemisorption or other possible interaction between a typically solid carrier and a compound being immobilised on the carrier. It is also contemplated that covalent bonds between a compound of formula (II) or formula (IV) can be formed in the complexes of the invention.

Any carrier can be used to form a complex with the bisphosphonate of formula (II) or the phosphonate group of the complex of formula (VI), as long as the complex that is formed is stable for its desired purpose. The carrier can be customized into any designs or shapes so that a drug for example, can be incorporated thereon or therein. The carrier can, for example be in the form of cement, ceramic blocks, ceramic beads, microbeads, granules, particulates, pellets, scaffolds, micro or macro porous material, injectable material in a polymeric carrier or combinations thereof. In some embodiments, the carrier can comprise an osteoconductive material. In other embodiments, the carrier can comprise an osteoconductive material and a structural support. Non-limiting examples of such carriers can for example include, hydroxyapatite $(Ca_{10}(PO_4)_6(OH)_2)$ or suitable precursors thereof; calcium sulphate; calcium phosphate; dicalcium phosphate; tricalcium phosphate; β-tricalcium phosphate (β-$Ca_3PO_4$); mono or biphasic calcium phosphates; composites of calcium sulphate and hydroxyapatite (PerOssal®); composites of hydroxyapatite; plaster of Paris and chitosan; calcium deficient apatite $(Ca_{10-x}(PO_4)_{6-x}(HPO_4)_x(OH)_{2-x})$ or combinations thereof (see Krisanapiboon A. et al, *Journal of Orthopaedic Surgery*, 2006, 14(3): 315-8; Shinto Y. et al, *The Journal of Bone and Joint Surgery*, 1992; 74-B: 600-4; Rauschmann M. A. et al, *Biomaterials*, 2005, 26:2677-2684; Sunder M. et al, *Trends Biomater. Artif Organs*, 2005, 18(2): 213-218.

In some embodiments, the carrier can comprise a coating using any of the carrier material described above, for example calcium phosphate or hydroxyapatite. In this context, the carrier can be used to coat a polymeric carrier or a liposome for example. Any polymeric material that is within the knowledge of the average skilled person can be used for this purpose. Such polymeric material can be of linear or branched polymers, homopolymers, blockpolymers, copolymers, or mixtures thereof. Examples of such polymeric material can include but are not limited to poly(lactide-co-glycide) (PLG), polymethylacrylate (PMMA), polyethylene glycol (PEG), poly(propylene glycol-fumerate), polylactic acid (PLA), or combinations thereof. Methods for coating a polymeric carrier, for example a microsphere or a liposome are known to the person of average skilled in the art and can also be described in for example, Jongpaiboonkit L., *Advanced Materials*, 2009, 21: 1960-1963 and Xu Q G, Tanaka Y, Czernuszka J T (2007), Encapsulation and release of a hydrophobic drug from hydroxyapatite coated liposomes. *Biomaterials*, 28, 2687-2694. Such a carrier can also include a drug or a pharmaceutically active compound to be targeted to the bone.

In line with the above, a complex of the invention can include an additional medicament or drug. Such a drug or medicament can be incorporated into or onto the carrier of the complexes of formula (I) or formula (VI) using methods that are known to persons of average skill in the art. These methods can include but are not limited to mixing, dissolving, granulating, entrapping, encapsulating, loading and impregnation methods (Rauschmann M. A. et al, *Biomaterials*, 2005, 26:2677-2684). As an illustrative example, when a hydroxyapatite is used as a carrier in the complex of the invention, a drug can for example be incorporated into the hydroxyapatite precursor mixture prior to the co-precipitation of the hydroxyapatite and the drug. Alternatively, when desired, the carrier can be used as a coating.

Any drug or medicament can be incorporated into the complex of the invention as long as the desired purpose is achieved. The term "drug" as used herein refers to any therapeutically active agent and is generally accepted in the art to be any compound or substance which is used to treat any given disease or disorder. In some embodiments, the drug can be an antibiotic, an antifungal, a peptide, a protein, a polymer, a nucleic acid molecule, or combinations thereof. Exemplary antibiotics can include but are not limited to vancomycin, gentamicin, amoxicillin, imipenem, amphotericin B, cefoperazone, doxycycline and combinations thereof, to mention only a few.

In certain embodiments, the complexes of the present invention can have a dual function system, in which the carrier and the bisphosphonate/phosphate moiety are both pharmaceutically active. In other embodiments, either the carrier or the bisphosphonate/phosphonate moiety can be pharmaceutically active. The term "pharmaceutically active" as used herein refers to any substance which is useful in the treatment or prevention of disease or disorder or in the regulation of a physiological condition in a human or animal subject.

In the compound of formula II, the term "alkyl", alone or in combination, refers to a fully saturated aliphatic hydrocarbon such as a straight or branched chain hydrocarbon group. The alkyl can for example be optionally substituted. In certain embodiments, an alkyl can comprise 1 to 20 carbon atoms, 1 to 15 carbon atoms, 1 to 10 carbon atoms, 1 to 8 carbon atoms, 1 to 6 carbon atoms, or 1 to 3 carbon atoms, wherein (whenever it appears herein in any of the definitions given below) a numerical range, such as "1 to 20" or "$C_1$-$C_{20}$", refers to each integer in the given range, e.g. "$C_1$-$C_{20}$ alkyl" means that an alkyl group comprising only 1 carbon atom, or 2 carbon atoms, or 3 carbon atoms, or 4 carbon atoms, or 5 carbon atoms, or 6 carbon atoms, or 7 carbon atoms, or 8 carbon atoms, etc., up to and including 20 carbon atoms. Examples of alkyl groups include, but are not limited to, methyl, ethyl, propyl, n-propyl, isopropyl, butyl, n-butyl, isobutyl, sec-butyl, tert-butyl, tert-amyl, pentyl, hexyl, heptyl, octyl, nonyl, decyl, undecyl, dodecyl, tridecyl, tetradecyl and pentadecyl and the like.

The term "alkenyl" as used herein refers to an alkyl group that contains in the straight or branched hydrocarbon chain one or more double bonds. In certain embodiments, an alkenyl comprises 0 to 6 carbon atoms, for example 2 to 6 carbon atoms, 2 to 5 carbon atoms or 2 to 4 carbon atoms, wherein a numerical range, such as "2 to 6" or "$C_2$-$C_6$", refers to each integer in the given range, e.g. "$C_2$-$C_6$ alkenyl" means that an alkenyl group comprising 2 carbon atoms, 3 carbon atoms, etc., up to and including 6 carbon atoms. An alkenyl used in this invention can for example be optionally substituted. Examples of alkenyl groups include, but are not limited to, ethenyl, propenyl, butenyl, 1,4-butadienyl, pentenyl, 4-methylhex-1-enyl, 4-ethyl-2-methylhex-1-enyl and the like.

The term "alkynyl" as used herein refers to an alkyl group that contains in the straight or branched hydrocarbon chain one or more triple bonds. In certain embodiments, an alkynyl comprises 0 to 6 carbon atoms, for example 2 to 6 carbon atoms, 2 to 5 carbon atoms, or 2 to 4 carbon atoms, wherein a numerical range, such as "2 to 6" or "$C_2$-$C_6$", refers to each integer in the given range, e.g. "$C_2$-$C_6$ alkynyl" means that an alkynyl group comprising 2 carbon atoms, 3 carbon atoms, etc., up to and including 6 carbon atoms. An alkynyl group of this invention may be optionally substituted. Examples of alkynyl groups include, but are not limited to, ethynyl, propynyl, butyryl, and the like.

The term "acyl" as used herein refers to a group having the formula —RC(=O). An acyl group used in the present invention can for example be optionally substituted. In certain embodiments, an acyl group comprises 1 to 6 carbon atoms, for example 1 to 5 carbon atoms, 1 to 4 carbon atoms, or 1 to 3 carbon atoms, wherein a numerical range, such as "1 to 20" or "$C_1$-$C_{20}$", refers to each integer in the given range, e.g. "$C_1$-$C_6$ acyl" means that an acyl group comprising 2 carbon atoms, 3 carbon atoms, etc., up to and including 6 carbon atoms. Examples of acyl groups include, but are not limited to formyl, acetyl, propanoyl, 2-methylpropanoyl, butanoyl and the like.

The term "cycloalkyl" refers to a completely saturated hydrocarbon ring. The cycloalkyl group used in this invention may range from $C_3$ to $C_8$. A cycloalkyl group of this invention can for example be optionally substituted. Examples of cycloalkyl groups include, but are not limited to cyclopropyl, cyclobutyl, cyclopentyl, cyclohexyl and the like.

The term "cycloalkenyl" as used herein refers to a cycloalkyl group that contains one or more double bonds in the ring although, if there is more than one, they cannot form a fully delocalized pi-electron system in the ring (otherwise the group would be "aryl" as defined herein). Cycloalkyl groups of this invention may range from $C_3$ to $C_8$. A cycloalkenyl group use in this invention may for example be optionally substituted. Examples of cycloalkenyl groups include, but are not limited to cyclohexenyl, cyclohepta-1,3-dienyl, cyclopropenyl, cyclobutenyl, cyclopentenyl, cyclohexenyl, cycloheptenyl and the like.

In the compound of formula (II), each of $L_1$ and $L_2$ is a linker having a main chain. The main chain can include 0, 1, 2, 3, 4, 5, 6, 7, 8, 9, 10, 11, 12, 13, 14, 15, 16, 17, 18, 19 and 20 main chain atoms. In this context, when the linker has 0 main chain atoms, an aminobisphosphonate of the formula $CH(PO_3H_2)_2NH_2$ as described in Uludag H., *Current Pharmaceutical Design*, 2002, 8(21): 1929-1944, can be used in the compound of formula (II) ( ). The main chain can contain an aliphatic and/or non-aliphatic moiety as long as the main chain includes 0 to 20 main chain atoms. The main chain of linkers $L_1$ and $L_2$ can be independently selected from the group consisting of optionally substituted $C_1$-$C_{20}$ alkyl, $C_1$-$C_{15}$ alkyl, optionally substituted $C_0$-$C_6$ alkenyl, optionally substituted $C_0$-$C_6$ alkynyl, optionally substituted $C_0$-$C_6$ acyl, optionally substituted aryl, optionally substituted heteroaryl, optionally substituted $C_{3-8}$ cycloalkyl, and optionally substituted $C_{3-8}$ cycloalkenyl. In case the linker comprises a cyclic structure such as cyclohexyl or phenyl, the number of main chains is counted such that the least number of atoms in the ring is obtained. That is, a cyclohexyl for example, is counted to contribute 4 main chain atoms to the linker $L_1$ or $L_2$; a cycloheptyl is counted to contribute 4 main chain atoms to the respective linker; and a cyclooctyl contributes 5 main chain atoms to the linker.

The main chain atoms can be a carbon or a heteroatom. The term "heteroatom" refers to an atom other than carbon or hydrogen. Heteroatoms are typically independently selected from oxygen, sulphur, nitrogen, and phosphorus, but are not limited to those atoms. In embodiments in which two or more heteroatoms are present, the two or more heteroatoms may all be the same as one another, or some or all of the two or more heteroatoms may each be different from the others. Thus, the linker can comprise an ether moiety, a polyoyether moiety, a thioether moiety, an amine moiety, or an amide moiety to mention only some illustrative examples.

The term "aryl" refers to an aromatic ring wherein each of the atoms forming the aromatic ring is a carbon atom. Aryl rings may be formed by five, six, seven, eight, nine, or more than nine carbon atoms. The aryl ring also includes biphenyl ring for example. Aryl groups may be optionally substituted. The term "aromatic" refers to a group comprising a covalently closed planar ring having a delocalized [pi]-electron system comprising 4n+2 [pi] electrons, where n is an integer. Aromatic may be formed by five, six, seven, eight, nine, or more than nine atoms. Aromatics or aryls may be optionally substituted. Examples of aryl or aromatic groups include, but are not limited to phenyl, naphthalenyl, phenanthrenyl, anthracenyl, tetralinyl, fluorenyl, indenyl, and indanyl. The term aromatic also includes, for example, benzenoid groups, connected via one of the ring-forming carbon, atoms, and optionally carrying one or more substituents selected from an aryl, a heteroaryl, a. cycloalkyl, a non-aromatic heterocycle, a halo, a hydroxy, an amino, a cyano, a nitro, an alkylamido, an acyl, a $C_1$-$C_6$ alkoxy, a $C_1$-$C_6$ alkyl, a $C_1$-$C_6$ aminoalkyl, alkylamino, an alkylsulfenyl, an alkylsulfinyl, an alkylsulfonyl, an sulfamoyl, or a trifluoromethyl. In certain embodiments, an aromatic or aryl group is substituted at one or more of the para, meta, and/or ortho positions. Examples of aryl or aromatic groups comprising substitutions include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl, 3-cyanophenyl, 4-cyanophenyl, dimethylphenyl, naphthyl, hydroxynaphthyl, hydroxymethylphenyl, (trifluoromethyl) phenyl, alkoxyphenyl, 4-morpholin-4-ylphenyl, 4-pyrrolidin-1-ylphenyl, 4-pyrazolylphenyl, 4-triazolylphenyl, and 4-(2-oxopyrrolidin-1-yl)phenyl, N—($C_1$-$C_6$alkyl)amino substituted aryl or N,N—($C_1$-$C_6$alkyl)amino aryl.

The term "optionally substituted" refers to a group in which none, one, or more than one of the hydrogen atoms has been replaced with one or more group(s) are independently selected from: alkyl, heteroalkyl, haloalkyl, heterohaloalkyl, cycloalkyl, aryl, arylalkyl, heteroaryl, non-aromatic heterocycle, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups.

The term "alkoxy", alone or in combination, refers to an aliphatic hydrocarbon having an alkyl-O-moiety. In certain embodiments, alkoxy groups are optionally substituted. Examples of alkoxy groups include, but are not limited to, methoxy, ethoxy, propoxy, butoxy and the like.

The term "arylalkyl" refers to a group comprising an aryl group bound to an alkyl group.

The term "heteroaryl" refers to an aromatic heterocycle. Heteroaryl rings may be formed by three, four, five, six, seven, eight, nine, or more than nine atoms. Heteroaryl rings may also be fused to at least one ring to form a part of a ring system. The term "ring system" refers to two or more rings, wherein two or more of the rings are fused. The term "fused" refers to structures which two or more rings share one or more bonds. Heteroaryls may be optionally substituted. Examples of heteroaryl groups include, but are not limited to, aromatic $C_{3-8}$ heterocyclic groups comprising one oxygen or sulfur atom or up to four nitrogen atoms, or a combination of one oxygen or sulfur atom and up to two nitrogen atoms, and their substituted as well as benzo- and pyrido-fused derivatives, for example, connected via one of the ring-forming carbon atoms.

The term "non-aromatic heterocycle" refers to a group comprising a non-aromatic ring wherein one or more atoms forming the ring is a heteroatom. Non-aromatic heterocyclic rings may be formed by three, four, five, six, seven, eight, nine, or more than nine atoms. Non-aromatic heterocycles may be optionally substituted or may be fused to one ring to form a ring system. In certain embodiments, non-aromatic heterocycles comprise one or more carbonyl or thiocarbonyl groups such as, for example, oxo- and thio-containing groups. Examples of non-aromatic heterocycles include, but are not limited to, lactams, lactones, cyclic imides, cyclic thioimides, cyclic carbamates, tetrahydrothiopyran, 4H-pyran, tetrahydropyran, 1,3-dioxane, 1,4-dioxin, 1,4-dioxane, piperazine, 1,3-oxathiane, 1,4-oxathiane, tetrahydro-1,4-thiazine, 2H-1, 2-oxazine, maleimide, succinimide, barbituric acid, thiobarbituric acid, dioxopiperazine, hydantom, dihydrouracil, morphinone, trioxane, hexahydro-1,3,5-triazine, tetrahydrothiophene, tetrahydrofuran, pyrroline, pyrrolidine, pyridone, pyrrohdione, pyrazone, pyrazolidme, imidazoline, imidazolidine, 1,3-dioxole, 1,3-dioxolane, 1,3-dithiole, 1,3-dithiolane, isoxazoline, isoxazolidine, oxazoline, oxazolidine, oxazolidone, thiazoline, thiazolidine, and 1,3-oxathiolane.

The term "heterocycle" refers to a group comprising a covalently closed ring wherein at least one atom forming the ring is a carbon atom and at least one atom forming the ring is a heteroatom. Heterocyclic rings may be formed by three, four, five, six, seven, eight, nine, or more than nine atoms. Any number of those atoms may be heteroatoms (i.e., a heterocyclic ring may comprise one, two, three, four, five, six, seven, eight, nine, or more than nine heteroatoms). Herein, whenever the number of carbon atoms in a heterocycle is indicated (e.g., $C_1$-$C_6$ heterocycle), at least one other atom (the heteroatom) must be present in the ring. Designations such as "$C_1$-$C_6$ heterocycle" refer only to the number of carbon atoms in the ring and do not refer to the total number of atoms in the ring. It is understood that the heterocylic ring will have additional heteroatoms in the ring. In heterocycles comprising two or more heteroatoms, those two or more heteroatoms may be the same or different from one another. Heterocycles may be optionally substituted. Binding to a heterocycle can be at a heteroatom or via a carbon atom. Examples of heterocycles include, but are not limited to the following:

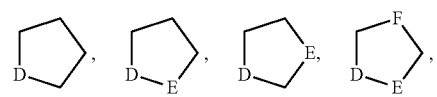

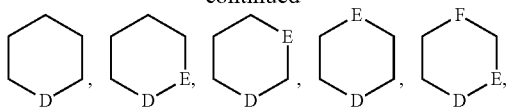 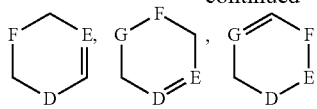

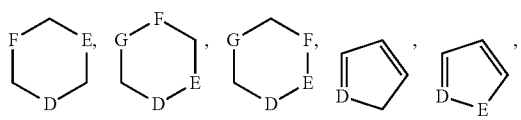

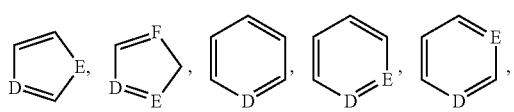

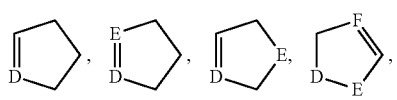

wherein D, E, F, and G independently represents a heteroatom. Each of D, E, F, and G may be the same or different from one another.

In certain illustrative embodiments, the linkers $L_1$ and $L_2$ can be one of N-methylamine benzene (CAS Number: 2739-12-0), N-ethylamino benzene (CAS Number 103-69-5), N,N-diethylbenzene amine (CAS Number: 91-66-7), N,N-dimethylamino benzene (CAS Number: 121-69-7), ethyl, propyl or pentyl, for example. In other embodiments, the linker can be an optionally substituted heteroaryl, for example an optionally substituted $C_1$-$C_8$ or $C_3$-$C_8$ heterocycle comprising at least one of nitrogen, oxygen or sulphur. Examples of such heterocycles can include any of the heterocycles as described herein and can also include 3-ethylpyridine (CAS Number: 537-78-7) and 1-ethylimidazole (CAS Number: 7098-07-9). When desired, an amino group can be introduced into the heterocycles by amination of nitrogen-containing heterocycles, in order to form a linkage, for example an amide bond with another bisphosphate compound. Such amination reactions are within the knowledge of persons of average skill in the art and include the established 'Chichibabin' amination reaction of an optionally substituted pyridine such as 3-ethylpyridine (U.S. Pat. No. 5,003,069). Other amination reactions can also be employed for example N-amination of pyrrole or indole heterocycles using monocholoroamine (Hynes Jr. J et al, *J. Org. Chem.*, 2004, 69, 1368-1371).

In some embodiments, the complex according to the present invention can be

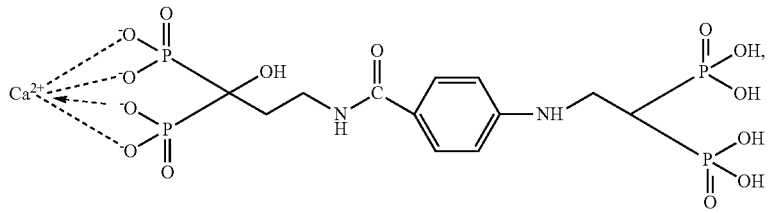

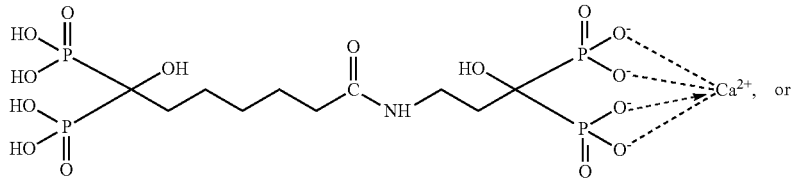

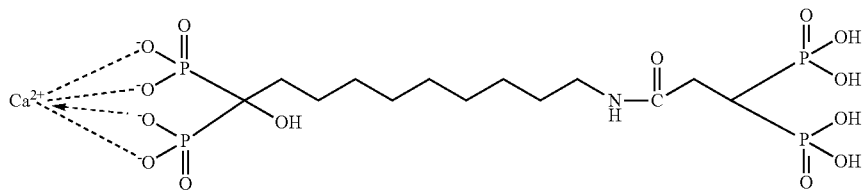

In other embodiments, the complex of the invention can be

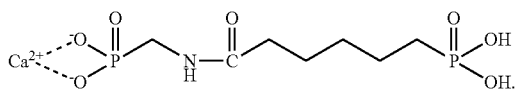

In certain embodiments the complex according to the invention can also include a radioactive element or a radioisotope. The radioisotope can for example, conjugate to the bisphosphonate or phosphonate moiety of the complexes of the present invention by forming a coordination or metal complex. Examples of such radioactive elements that can be used can include $^{99m}$Tc, $^{153}$Sm, $^{131}$I, $^{123}$I, $^{186}$Re and $^{211}$At. Methods for conjugating a radioisotope to a bisphosphonate are within the knowledge of the person of average skill in the art and can also be described in Neves M. et al, Synthesis, characterization and biodistribution of bisphosphonates Sm-153 complexes: correlation with molecular modeling interaction studies, Nuc. Med. & Biol., 2002, 29(3): 329-338; Ogawa K, Mukai T, Asano D, Kawashima H, Kinuya S, Shiba K, Hashimoto K, Mori H, Saji H. J. Nucl Med. 2007, January; 48(1):122-7; and Larsen R H, Murud K M, Akabani G, Hoff P, Bruland O S, Zalutsky M R, 211At- and 131I-labeled bisphosphonates with high in vivo stability and bone accumulation, J. Nucl Med. 1999, July; 40(7):1197-203.

The present invention also provides a method of treatment or prevention of a bone-related disease or disorder. The method includes administering a pharmaceutically active amount of a complex of formula (I) or (VI) of the invention to a subject in need thereof. The invention also provides a complex or a pharmaceutical composition or medicament thereof for use in the treatment or prevention of a bone-related disease or disorder. The term "to treat" as used herein is intended to refer to providing an pharmaceutically amount of a complex of the invention or a respective pharmaceutical composition or medicament thereof sufficient to act prophylactically to prevent the development of a weakened and/or unhealthy state; and/or providing a subject with a sufficient amount of the complex or pharmaceutical composition or medicament thereof so as to alleviate or eliminate a disease state and/or the symptoms of a disease state, and a weakened and/or unhealthy state.

The term "bone-related diseases or disorders" can in some embodiments refer to patients having poor bone mineral density. In other embodiments, bone-related diseases or disorders can include diseases that affect the bone. Non-limiting examples of such bone-related diseases or disorders can include osteoporosis, osteomyelitis, osteitis deformans ("Paget's disease of bone"), bone metastasis, multiple myeloma, primary hyperparathyroidism and osteogenesis imperfecta.

As used herein, the term "subject" refers to animals such as mammals, including, but not limited to, primates (e.g., humans), cows, sheep, goats, horses, dogs, cats, rabbits, rats, mice and the like. In certain embodiments, the subject is a human.

A complex of the present invention or a pharmaceutically active amount thereof, can be administered as a subject, for example a human patient or can be administered in pharmaceutical compositions in which the foregoing materials are mixed with suitable carriers or excipient(s). Techniques for formulation and administration of drugs may be found in "Remington's Pharmacological Sciences," Mack Publishing Co., Easton, Pa., latest edition.

As used herein, "administer" or "administration" refers to the delivery of a complex of formula (I) or a pharmaceutical composition or medicament containing a complex of formula (I) of the invention to a subject for the purpose of prevention or treatment of a bone-related disease or disorder.

Suitable routes of administration may include, without limitation, oral, rectal, transmucosal or intestinal administration or intramuscular, subcutaneous, intramedullary, intrathecal, direct intraventricular, intravenous, intravitreal, intraperitoneal, intranasal, or intraocular injections. Alternatively, one may administer the complex or a respective pharmaceutical composition or medicament, in a local rather than systemic manner, for example, via injection of the compound directly into a vessel, optionally in a depot or sustained release formulation.

Pharmaceutical compositions of the present invention may be manufactured by processes well known in the art, for example, by means of conventional mixing, dissolving, granulating, drageemaking, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the complex of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the complexes of the invention can be formulated by combining the active compounds with pharmaceutically acceptable carriers well known in the art. Such carriers enable the compounds of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatine, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatine, as well as soft, sealed capsules made of gelatine and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, or liquid polyethylene glycols. Stabilizers may be added in these formulations, also.

The complexes of the present invention may also be formulated for parenteral administration, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, without limitation, a salt, of the complex.

Additionally, suspensions of the complexes may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextrane. Optionally, the suspension may also contain suitable stabilizers and/or agents that increase the solubility of the compounds to allow for the preparation of highly concentrated solutions.

Alternatively, the complex may be in powder form for constitution with a suitable vehicle, e.g., sterile, pyrogen-free water, before use.

The complexes may also be formulated in rectal compositions such as suppositories or retention enemas, using, e.g., conventional suppository bases such as cocoa butter or other glycerides.

In addition to the formulations described previously, the complexes may also be formulated as depot preparations. Such long acting formulations may be administered by implantation (for example, subcutaneously or intramuscularly) or by intramuscular injection. A complex of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

A non-limiting example of a pharmaceutical carrier for the complexes of the invention is a cosolvent system comprising benzyl alcohol, a nonpolar surfactant, a water-miscible organic polymer and an aqueous phase such as the VPD co-solvent system. VPD is a solution of 3% w/v benzyl alcohol, 8% w/v of the nonpolar surfactant Polysorbate 80, and 65% w/v polyethylene glycol 300, made up to volume in absolute ethanol. The VPD co-solvent system (VPD: D5W) consists of VPD diluted 1:1 with a 5% dextrose in water solution. This cosolvent system dissolves hydrophobic compounds well, and itself produces low toxicity upon systemic administration.

Naturally, the proportions of such a co-solvent system may be varied considerably without destroying its solubility and toxicity characteristics. Furthermore, the identity of the co-solvent components may be varied: for example, other low toxicity nonpolar surfactants may be used instead of Polysorbate 80, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for the pharmaceutical complexes may be employed such as liposomes and emulsions. In addition, certain organic solvents such as dimethylsulfoxide also may be employed, although often at the cost of greater toxicity.

Additionally, the complexes may be delivered using a sustained-release system, such as semipermeable matrices of solid hydrophobic polymers containing the complex. Various sustained-release materials have been established and are well known by those skilled in the art. Sustained-release capsules may, depending on their chemical nature, release the complexes or the active ingredients for a few weeks up to over 100 days. Depending on the chemical nature and the biological stability of the therapeutic reagent, additional strategies for stabilization may be employed.

The pharmaceutical compositions herein also may comprise suitable solid or gel phase carriers or excipients. Examples of such carriers or excipients include, but are not limited to, calcium carbonate, calcium phosphate, various sugars, starch, cellulose derivatives, gelatine, and polymers such as polyethylene glycols.

Many of the complexes of the invention may be provided as physiologically acceptable salts wherein the complexes may form the negatively or the positively charged species. Examples of salts in which the complex forms the positively charged moiety include, without limitation, the sodium, potassium, calcium and magnesium salts formed by the reaction of a phosphonic acid group in the compound with an appropriate base (e.g. sodium hydroxide (NaOH), potassium hydroxide (KOH), Calcium hydroxide (Ca(OH)$_2$), etc.).

Pharmaceutical compositions suitable for use in the present invention include compositions wherein the active ingredients are contained in an amount sufficient to achieve the intended purpose, e.g., the treatment or prevention of a bone related disorder or disease.

More specifically, a therapeutically effective amount means an amount of compound effective to prevent, alleviate or ameliorate symptoms of bone-related disease or disorder or prolong the survival of the subject being treated.

Determination of a therapeutically effective amount is well within the capability of those skilled in the art, especially in light of the detailed disclosure provided herein.

For any complexes used in the methods of the invention, the therapeutically effective amount or dose can be estimated initially from the described assays. Toxicity and therapeutic efficacy of the compounds or complexes described herein can be determined by standard pharmaceutical procedures in cell cultures or experimental animals, e.g., by determining the MIC and the $LD_{50}$ for a subject compound. The data obtained from these cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition.

Dosage amount and interval may be adjusted individually to provide plasma levels of the active species which are sufficient to exert the desired effect. These plasma levels are referred to as minimal effective concentrations (MECs).

Dosages necessary to achieve the MEC will depend on individual characteristics and route of administration. HPLC assays or bioassays can be used to determine plasma concentrations. Dosage intervals can also be determined using MEC value. Complexes should be administered using a regimen that maintains plasma levels above the MEC for 10-90% of the time, preferably between 30-90% and most preferably between 50-90%. In cases of local administration or selective uptake, the effective local concentration of the drug may not be related to plasma concentration and other procedures known in the art may be employed to determine the correct dosage amount and interval.

The amount of a composition or complex administered may, of course, be dependent on the subject being treated, the severity of the affliction, the manner of administration, the judgment of the prescribing physician, etc.

The compositions or complexes may, if desired, be presented in a pack or dispenser device, such as a kit approved by a regulatory authority, such as EMEA or FDA, which may contain one or more unit dosage forms containing the active ingredient. The pack may for example comprise metal or plastic foil, such as a blister pack. The pack or dispenser device may be accompanied by instructions for administration.

The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration.

Compositions comprising a compound of the invention formulated in a compatible pharmaceutical carrier may also be prepared, placed in an appropriate container, and labeled for treatment of an indicated condition.

As used herein, a "physiologically/pharmaceutically acceptable carrier" refers to a carrier or diluent that does not cause significant irritation to an organism and does not abrogate the biological activity and properties of the administered compound.

A "pharmaceutically acceptable carrier or excipient" refers to an inert substance added to a pharmaceutical composition to further facilitate administration of a compound. Examples, without limitation, of excipients include calcium carbonate, calcium phosphate, various sugars and types of starch, cellulose derivatives, gelatine, vegetable oils and polyethylene glycols.

Methods of preparing the complexes of the present invention are within the knowledge of the person of average skill in the art. When desired, the complex of the present invention can be prepared by using one bisphosphonate, two identical or different bisphosphonates, or more bisphosphontaes. In some embodiments, a method of preparing a complex of the present invention can include reacting a compound of formula (IIa) in which the carrier is bound onto a bisphosphonate

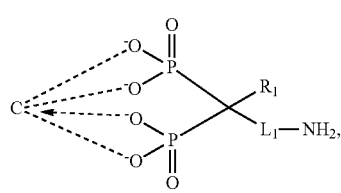

(IIa)

with a further (second) bisphosphonate compound, for example a bisphosphonate compound of formula (III),

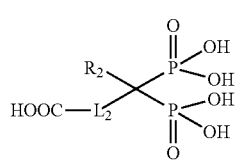

(III)

under conditions to form the complex of formula (I) (see also Example 3).

In other embodiments, only one type of bisphosphonate can be used to prepare the complex of the present invention. This can be done by reacting a bisphosphonate compound of formula (IV)

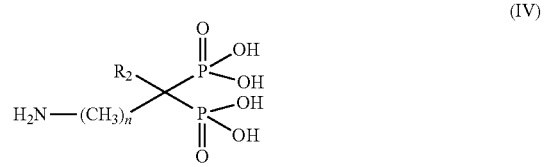

(IV)

with a compound of formula (V), $$X-(CH_3)_n-COOH \quad (V)$$

under conditions to form the compound of formula (III), wherein X is Br or F and n is an integer from 2 to 8. The compound of formula (III) can then react with the compound of formula (IV) in which the carrier is bound thereon, in order to form the complex of the invention.

As mentioned above, the invention also provides a complex of formula (VI) of a phosphonate compound of formula (VII) in which the complex is adapted to target a bone.

VII

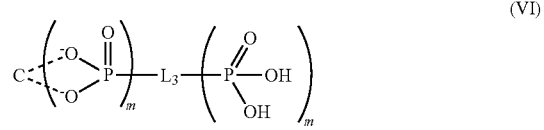

(VI)

In the complex of formula (VI), C represents a carrier to which the phosphonate compound is bound thereto. m can be an integer of 1, 2, 3, 4, 5, 6, 7, 8, 9, or 10. The carrier can be any of the carrier as described above and can include but is not limited to hydroxyapatite ($Ca_{10}(PO_4)_6(OH)_2$), calcium sulphate, hydroxyapatite composites of calcium sulphate and hydroxyapatite, hydroxyapatite composites of plaster of Paris, chitosan and hydroxyapatite, $\beta$-$Ca_3PO_4$, tricalcium phosphate, mono or biphasic calcium phosphate calcium deficient apatite ($Ca_{10-x}(PO_4)_{6-x}(HPO_4)_x(OH)_{2-x}$), a polymeric carrier coated with calcium phosphate and combinations thereof.

In the complex of formula (VI), $L_3$ is a linker typically having a main chain comprising 1 to 100 main chain atoms, 1 to 80 main chain atoms, 1 to 75 main chain atoms, 1 to 50 main chain atoms, 1 to 40 main chain atoms, 1 to 30 main chain atoms, or 1 to 20 main chain atoms. The main chain can be an aliphatic and/or non-aliphatic chain and can include 1, 2, 3, 4, 5, 6, 7, 8, 9, 10, 11, 12, 13, 14, 15, 16, 17, 18, 19, 20, 23, 24, 25, 26, 27, 28, 29, 30, 40, 50 or up to 100 main chain atoms. The main chain atoms can include carbon or heteroatom or both carbon and heteroatoms such as N, O, S, B, P for example. In certain embodiments, the linker $L_3$ can be one of optionally substituted $C_1$-$C_{20}$ alkyl, optionally substituted $C_2$-$C_{15}$ alkenyl, optionally substituted $C_2$-$C_{15}$ alkynyl, and a dendrimer.

In this context, a dendrimer refers to a hyperbranched, uniformly distributed structure, having definite molecular weight, shape and size. When a dendrimer is used as a linker $L_3$, any dendrimers can be used as long as the dendrimer provides for at least one phosphonate that can bind to the carrier at one location of the complex of formula (VI), and at least one free phosphonate moiety spaced apart, for example, at 'the other end' of the complex of formula (VI). The dendrimer can, for example, have the following schematic structure of scheme (1), in which at least 4, 5, 6, 7, 8, 9 or 10 phosphonates are present. This schematic structure can be symmetrically arranged in such an order that at least 2 phosphonate ($HO_2PO$) are bound to the carrier and at least two other free phosphonates are at the other end.

Scheme (1)

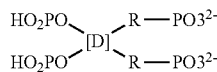

The illustrative structure of scheme (1) means that two of the phosphonate groups, say phosphonate group 1 and phosphonate group 2, are arranged such in the compound of formula (VII) that they are able to interact with the carrier (for example, to mimic a bisphosphonate group) while the phosphonate groups 3 and 4 are arranged such in the compound of formula (VII) such 1) that they are able to act as an accessible target group for later interaction with bone material and 2) at the same are spatially separated from the phosphonate groups 1 and 2 such they groups 3 and 4 do not interact with the carrier. The groups 3 and 4 can with respect to each other being arranged in the compound of formula (VII) that they mimic a bisphosphonate groups. In case, more than 4 phosphonate groups are present in a compound of formula (N), say for example, 6 groups, phosphonates groups 5 or 6 can either be arranged as a further pair (again mimicking a bisphosphonate group), either to interact with the carrier or be used as a targeting group. Alternatively, phosphonate group 5 can be arranged such in the compound of formula (VII) that is interacts together with the phosphonate groups 1 and 2 in the complexation of the carrier while phosphonate group 6 can be arranged such that is acts as accessible target phosphonate group. Likewise, further groups, for example, phosphonate group 7 and 8 can be arranged together or alone to interact with the carrier or to be available as targeting groups.

An exemplary embodiment of a compound of formula (VII) as illustrated in scheme (I) is a dendrimer having the following structure, when used as the linker ($L_3$) in the complex of formula (VI) of the present invention. In this compound of formula (VII), the R substituent can be replaced by a phosphonate for example, the dendrimer can have 24 main chain atoms, for example.

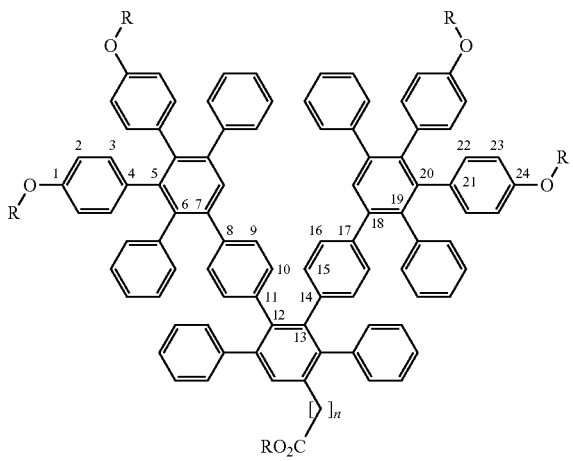

Methods for preparing such dendrimers are within the knowledge of a person of average skill in the art and are also described, for example, in Grimsdale A. C. et al, 2005, The Chemistry of Organic Nanomaterials, *Angew. Chem. Int. Ed.* 44, 5592-5629; Tomalia D. A., et al, A new class of polymer: starburst-dendritic macromolecules, 1985, Polym. J. 17, 117-132; and Zhuo R. X. et al., "In vitro release of 5-fluorouracil with cyclic core dendritic particles". J. Control Re. 57, 249-257. As a non-limiting illustrative example, a polyamidoamine (PAMAM) dendrimer can be synthesized by successive Michael addition and amidation reactions using ethylenediamine and methylmethacrylate. Such synthesis methods also described in Bhadra D. et al., 2003, Int. J. of Pharmaceutics, 257, 111-124. Other dendrimers can also be used in the present invention and include, but are not limited to, a polypropylene dendrimer, a polyethyleneimine dendrimer, a carbohydrate based dendrimer, a peptide based dendrimer, a glycopeptide dendrimer, a metal containing dendrimer, a poly aryl amine dendrimer, a polyamide dendrimer, a poly (alkyl amine) dendrimer, a polyamido alcohol dendrimer, a cyano dendrimer, a polyether dendrimer, a polythioether dendrimer, a polysiloxane dendrimer, a dendritic aryl ester, a perchlorinated dendrimer, a catalytic centre containing dendrimer, a silicon containing dendrimer, a phosphorus containing dendrimer, and a hydrocarbon dendrimer.

As mentioned above, a dendrimer used according to the present invention can be surface-modified with different functional groups for this purpose. The dendrimer can for example, be PEGylated by methods known to person skilled in the art (see for example, Bhadra D. et al., 2003, *Int. J. of Pharmaceutics*, 257, 111-124; Grimsdale A. C. et al, 2005, The Chemistry of Organic Nanomaterials, *Angew. Chem. Int. Ed.* 44, 5592-5629). Phosphonate functionalized dendrimers can also be synthesized through the route similar to dendrimer PEGylation methods, by attaching a phosphonate molecule instead of PEG. Alternative methods for preparing phosphonate functionalized dendrimers are also available to persons skilled in the art and are described for example, by Chen et al., *J. Am. Chem. Soc.,* 2004, 126, 10044-10048.

As mentioned above, one, two, or more phosphonate moieties can be attached to the linker $L_3$ in the complex of formula (VI).

In some embodiments, the linker $L_3$ can comprise of a main chain comprising up to 8, 9, 10, 11, or 12 main chain atoms in order to form a complex of formula (VI) of the present invention. Such a complex can for example, be prepared by reacting a hydroxyapatite bound to a phosphonate compound for example (modified hydroxyapatite), with another phosphonate compound using known coupling methods such as click chemistry or amide coupling methods (See FIGS., 4 to 6 and Examples 5 and 6). Examples of such a complex of formula (VI) can not only include the following complex in which the linker ($L_3$) consists of 8 main chain atoms, but also other complexes in which the linker ($L_3$) can contain 9, 10, 11, 12 or more main chain atoms, by using a respective heptyl, octyl, nonyl, or decyl moiety in the linker $L_3$. Examples of such a complex can include but are not limited to the following:

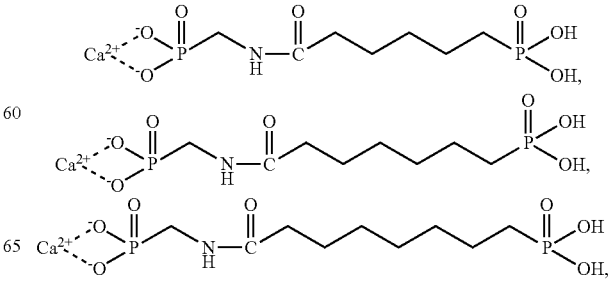

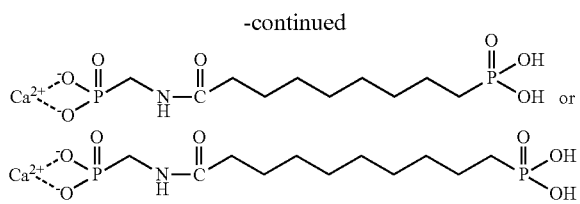

The above aspects of the present invention and the advantages will be more fully understood in view of the following description of the drawings and the non-limiting examples.

EXAMPLES

Example 1

Figure 1:
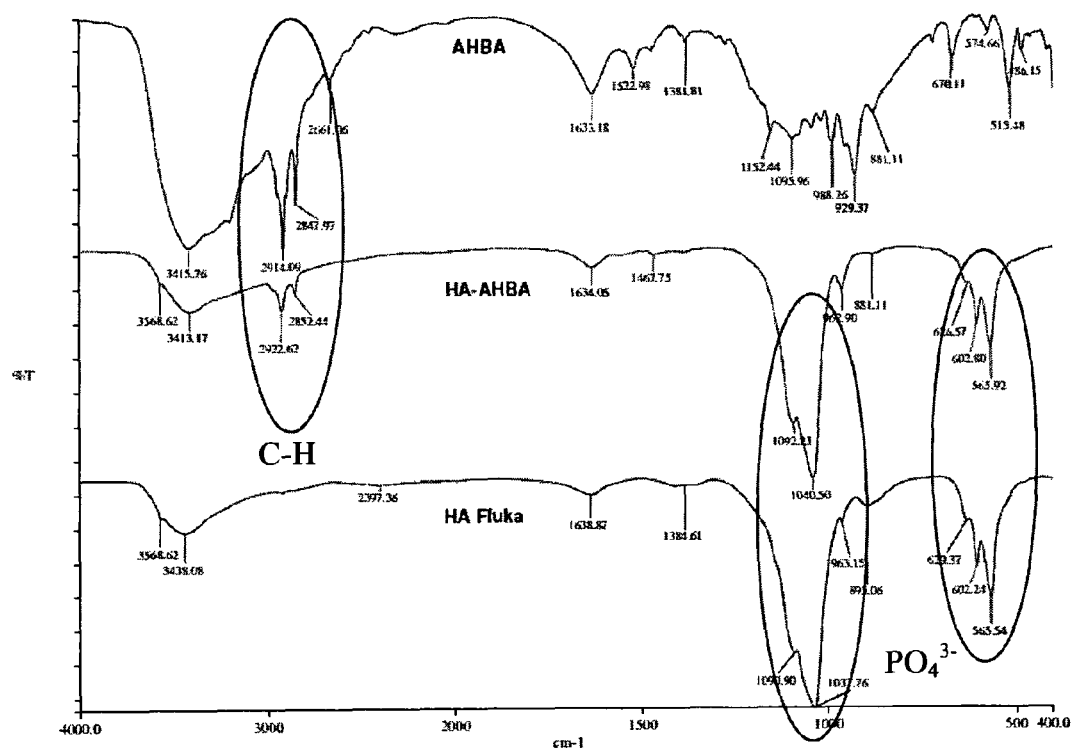
FIG. 1 shows a FTIR spectrum of 11-amino-1-hydroxyundecylidene-1,1-bisphosphonic acid (AHBA)-attached to hydroxyapatite (HA) obtained from Example 1. "HA-AHBA" represents the compound in which 11-amino-1-hydroxyundecylidene-1,1-bisphosphonic acid is attached to hydroxyapatite. "AHBA" represents 11-amino-1-hydroxyundecylidene-1,1-bisphosphonic acid alone and "HA Fluka" represents hydroxyapatite. The C—H and phosphate ($PO_4^{3-}$) peaks are indicated in the circles on the spectrum.
Figure 2:
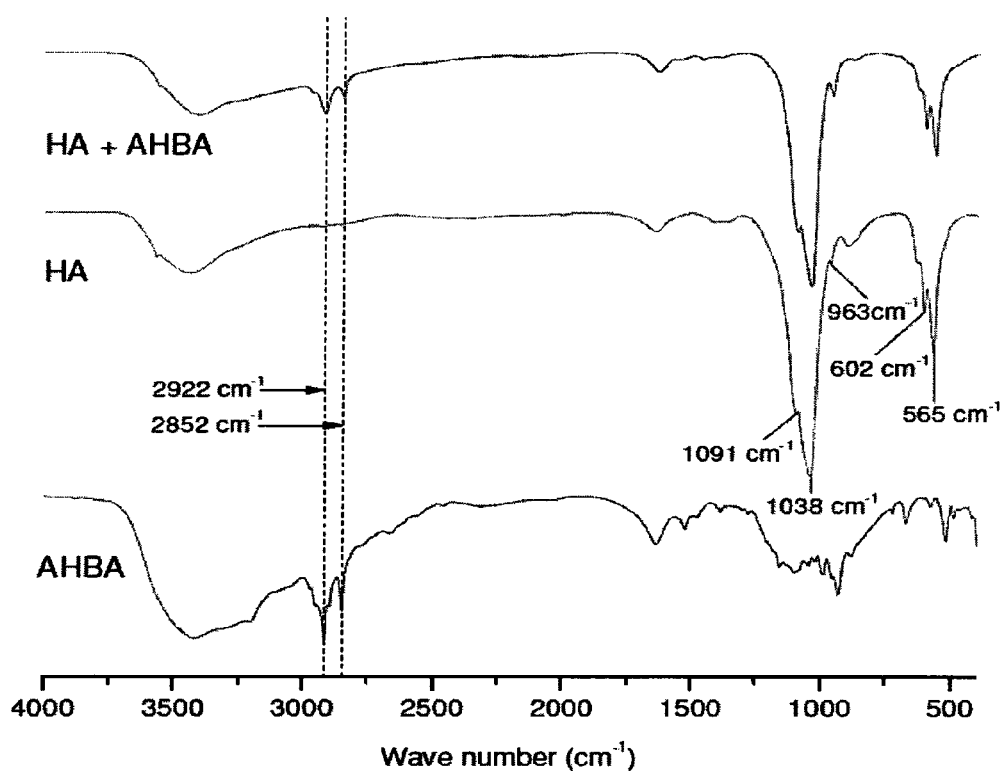
FIG. 2 shows another FTIR spectrum of 11-amino-1-hydroxyundecylidene-1,1-bisphosphonic acid (AHBA) attached to hydroxyapatite (HA) obtained from Example 1.
Figure 3:
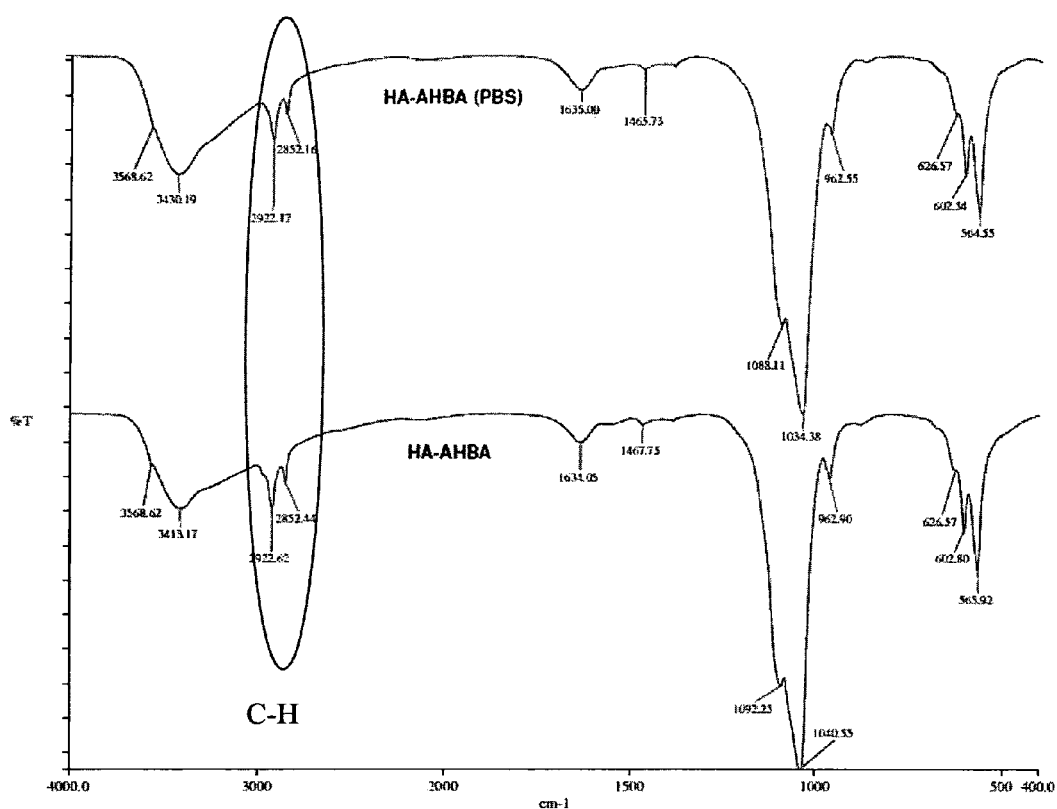
FIG. 3 shows a FTIR spectrum of HA-AHBA immersed in PBS (indicated as "HA-AHBA (PBS)") obtained from Example 2. There is no change in spectra between HA-AHBA (PBS) and HA-AHBA, showing stability of bisphosphonate attachment to HA nanoparticles.

11-amino-1-hydroxyundecylidene-1,1-bisphosphonic acid (AHBA) attachment onto hydroxyapatite (HA)

The present example illustrates the reaction between a bisphosphonate used according to an embodiment of the present invention, 11-amino-1-hydroxyundecylidene-1,1-bisphosphonic acid (AHBA), with hydroxyapatite.

5 mg of HA (Fluka) was suspended in 2 ml of deionized (DI) water. In a separate reaction mixture, 20 mg of finely ground AHBA was dissolved in 0.5 ml of sodium hydroxide, NaOH 1N. Subsequently, 0.5 ml of deionized water was added to the AHBA solution and heated gently. The AHBA solution was then filtered using 0.2 μm cellulose membrane filter. The HA suspension was mixed with the AHBA solution and stirred for 1 hour. The reaction mixture was centrifuged at 10000 rpm for 5 minutes and the supernatant was decanted. The pellet was redispersed with 3 ml of NaOH 1N and vortexed. The centrifugation and vortexing steps were repeated twice. After repeating these steps for two times in the presence of NaOH, the centrifugation and vortexing step was repeated for another three times in the presence of deionized water.

Example 2

Immersion of HA-AHBA in PBS

To ascertain the stability of bisphosphonate stability of bisphosphonate attachment into HA nanoparticles, 5 ml of PBS solution (pH=7.4) was added to the HA-AHBA formed in Example 1. The mixture was vortex and incubated at 150 rpm, 37° C. for 2 days. The incubated mixture was then centrifuged at 10000 rpm for 5 minutes and the supernatant was decanted. The pellet was redispersed with 3 ml of NaOH 1N and vortexed. The centrifugation and vortexing step was repeated for 2 times. After repeating these steps for two times in the presence of NaOH, the centrifugation and vortexing step was repeated for another three times in the presence of deionized water. The final product was frozen for 3 hours and then freeze-dried overnight.

Example 3

Amide bond formation of HA-AHBA and 4,4-diphosphonobutanoic acid (DPBA)

The present example illustrates the reaction between HA-AHBA obtained from Example 1 with a bisphosphonate used according to an embodiment of the present invention, 4,4-diphosphonobutanoic acid (DPBA).

5 mg of DPBA was dissolved in 5 ml of deionized water (1 mg/ml). 1-ethyl-3-(3-dimethylaminopropyl) carbodiimide (EDC) and NHS coupling agents were added to DPBA solution and stirred for 10 minutes. HA-AHBA that was obtained in Example 1 was added to the mixture solution and stirred for 1 hour. The reaction mixture was centrifuged at 10000 rpm for 5 minutes. The supernatant was decanted. The pellet was redispersed with deionized water and vortexed. The centrifugation and vortexing steps were repeated 3 times. After which, the final product was frozen for 3 hours and freeze-dried overnight.

Example 4

Amide bond formation of AHBA and DPBA (4,4-diphosphonobutanoic acid)

This example illustrates the reaction between AHBA and DPBA according to an embodiment of the present invention.

5 mg of DPBA was dissolved in 5 ml deionized (DI) water (1 mg/ml). EDC and NHS (coupling agents) were added to the DPBA solution and stirred for 10 minutes. In a separate solution, AHBA was dissolved in 0.5 ml NaOH 1N and 0.5 ml DI water. The AHBA solution was added to the mixture solution and stirred overnight. The final product was frozen for 3 hours and then freeze-dried overnight.

Example 5

Figure 4:
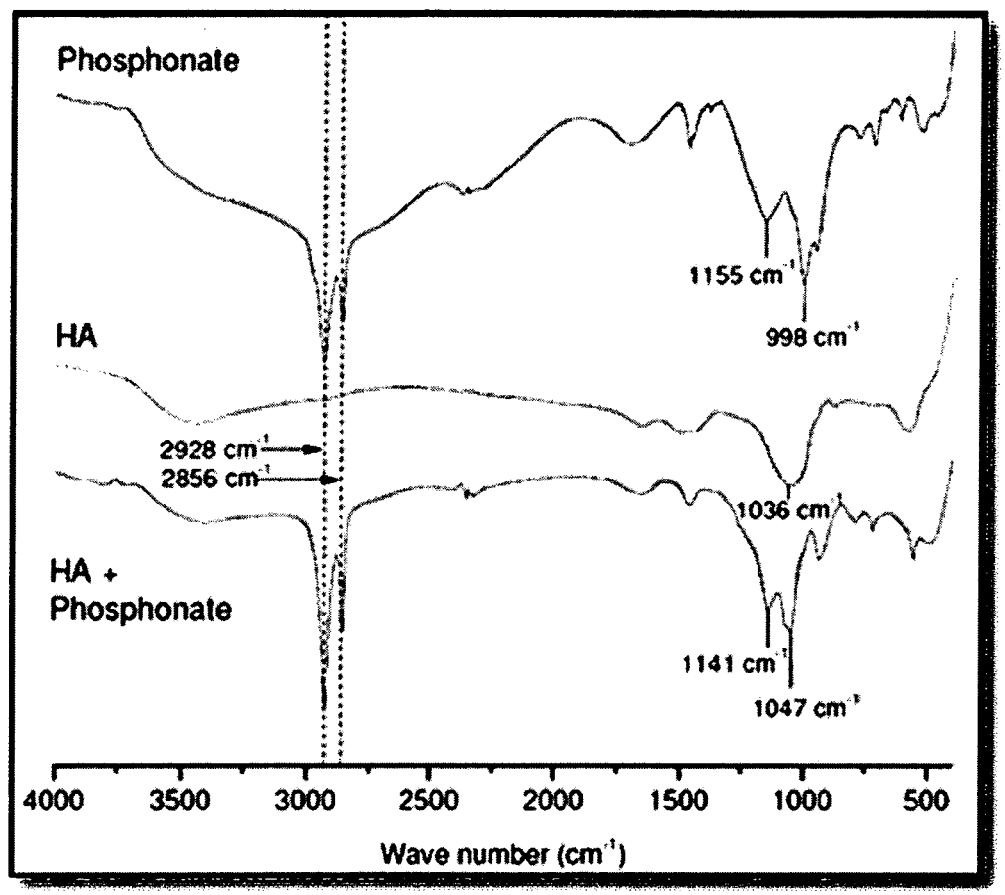
FIG. 4 shows a FTIR spectrum of (aminomethyl)phosphonic acid (AMPA) attached to hydroxyapatite (HA) as obtained in Example 5. "HA-Phosphonate" indicates the spectra of AMPA-HA.
Figure 5:
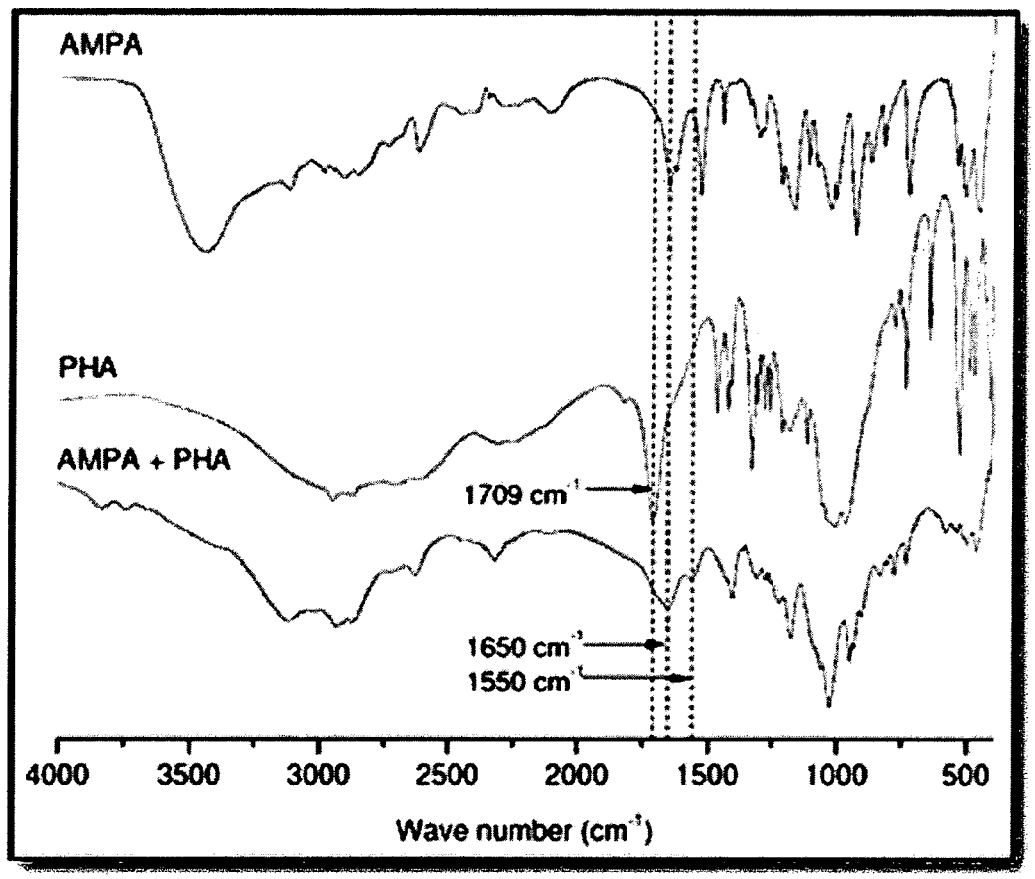
FIG. 5 shows a FTIR spectrum of the compound (aminomethyl)phosphonic acid (AMPA) coupled to 6-phosphonohexanoic acid (PHA) according to one embodiment of the invention.
Figure 6:
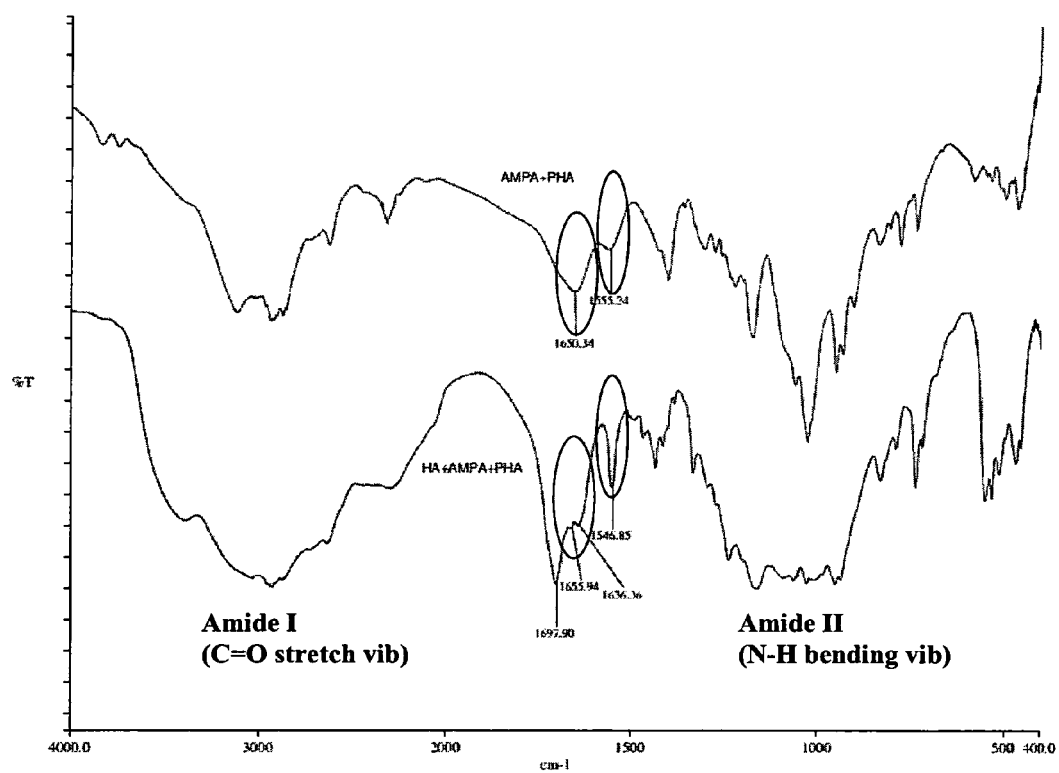
FIG. 6 shows a FTIR spectrum of a complex according to an embodiment of the invention, in which HA-AMPA obtained from Example 5 is coupled to PHA.
Figure 7:
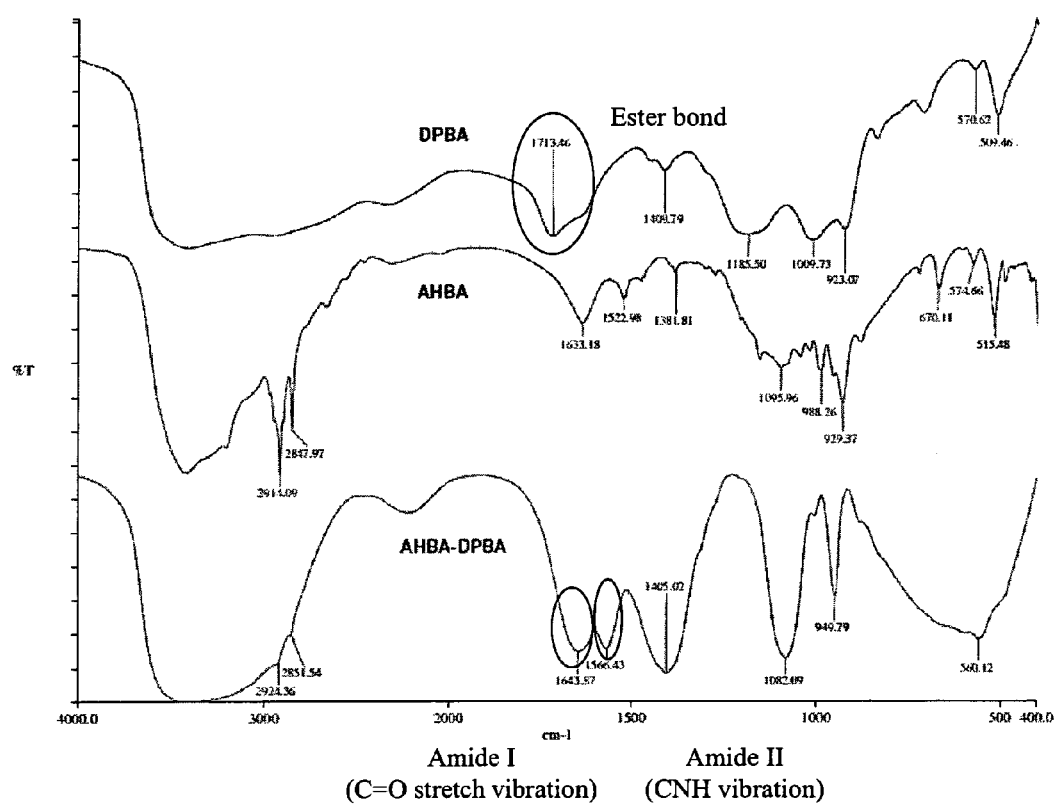
FIG. 7 shows amide bond formation of HA-AHBA and 4,4-diphosphonobutanoic acid (DPBA) as obtained in Example 3.
Figure 8:
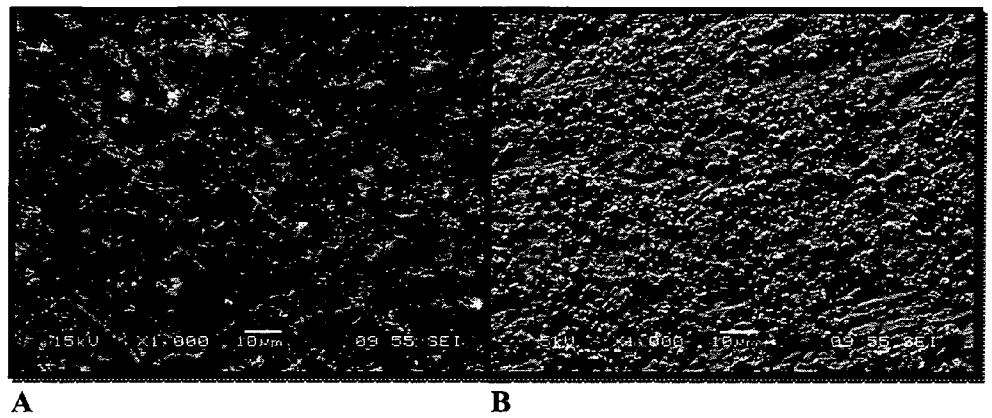
FIG. 8A shows a SEM image of bone slices used as a control.
FIG. 8B shows an image of a sample of bone slices treated or administered with the modified hydroxyapatite, HA-AHBA-DPBA, as obtained in Example 3.
Figure 9:
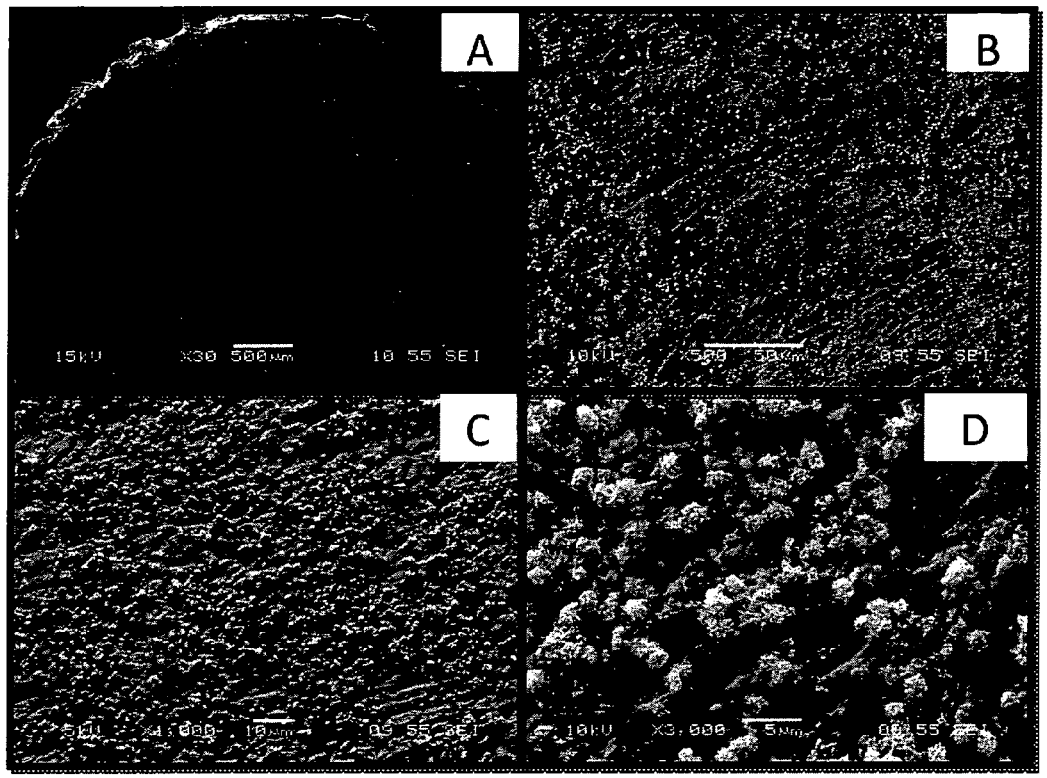
FIG. 9 shows SEM images of bone slices treated or administered with modified hydroxyapatite, HA-AHBA-DPBA, as obtained in Example 3. The images having a magnification ×30, ×500, ×1000 and ×3000 are indicated as FIGS. 9A, 9B, 9C and 9D respectively.
Figure 10:
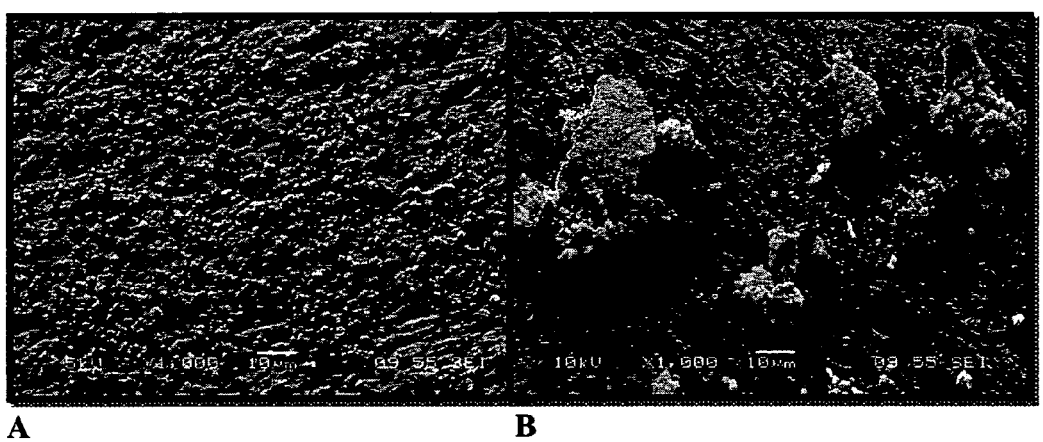
FIG. 10A shows a SEM image of bone slices treated or administered with modified hydroxyapatite, HA-AHBA-DPBA obtained in Example 3.
FIG. 10B shows an image of bone slices treated or administered with hydroxyapatite only.
Figure 11:
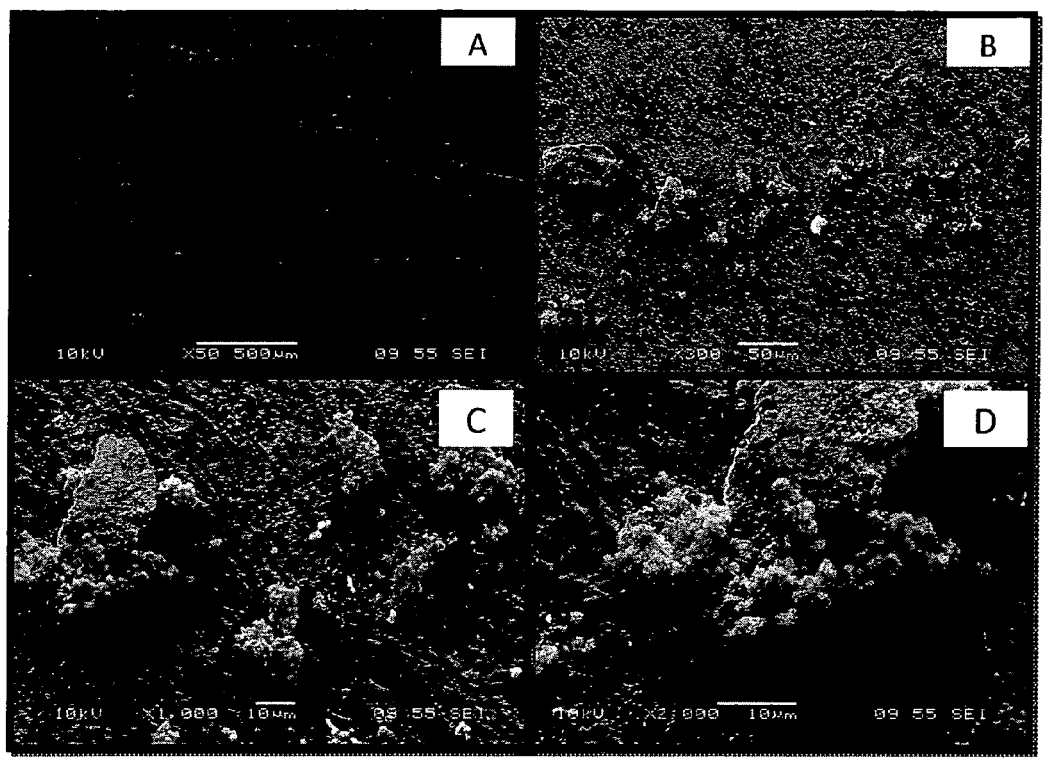
FIG. 11 shows SEM images of bone slices treated or administered with hydroxyapatite only (without bisphosphonate). The images having a magnification of ×50, ×300, ×1000 and ×2000 are indicated as FIGS. 11A, 11B, 11C and 11D respectively.

Attaching (Aminomethyl)phosphonic acid (AMPA) to hydroxyapatite (HA) to form HA-AMPA The present example illustrates the reaction between a bisphosphonate used according to an embodiment of the present invention, (aminomethyl)phosphonic acid (AMPA), with hydroxyapatite. In this example, the methodology used is similar to Example 1 with the exception that AMPA was used as the bisphosphonate instead of AHBA. The final product was analysed by FTIR (see Example 7) and illustrated in FIG. 4.

Example 6

Amide bond formation of HA-AMPA and 6-phosphonohexanoic acid (PHA)

The present example illustrates the reaction between HA-AHMA obtained from Example 5 with a bisphosphonate used according to an embodiment of the present invention, 6-phosphonohexanoic acid (PHA). The methodology used in this example is similar to Example 3 with the exception that HA-HAMA and PHA were used as reactants.

Example 7

Fourier Transform Infra-Red (FTIR)

To structurally analyse and identify the compounds and complexes obtained according to the invention, infrared spectra were obtained using the Perkin-Elmer system 2000 Fourier Transform Infra-Red (FTIR) spectrometry. For FTIR analysis, samples were ground together with oven-dried KBr powder and compressed into a disc. The FTIR spectra were obtained with 16 scans per disc over the range of 4000-400 $cm^{-1}$.

Example 8

HA-Bisphosphonate Nanoparticles Showing Accumulation in Bone Slices 10 mg of HA-particle was suspended in 15 ml of DI water. At the same time, 5 mg of AHBA-DPBA was dissolved in 3 ml of DI water and sonicated for about 2 min. Both solutions were mixed and stirred overnight at 800 rpm. The mixture was then washed by centrifugation 3 times using DI water. 1 ml of DI water was subsequently added to the final washed precipitate and vortexed before use. Bone slices, of animal origin, were introduced to the 1 ml solution (HA-AHBA-DPBA) and incubated for 1 hour. HA particles without bisphosphonate attached were used as control. After which, the bone slices were washed by immersion in DI water for 5 min. They were subsequently placed on filter paper to remove excess water before SEM observation.

The listing or discussion of a previously published document in this specification should not necessarily be taken as an acknowledgement that the document is part of the state of the art or is common general knowledge. All documents listed are hereby incorporated herein by reference in their entirety.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognise that the invention is also thereby described in terms of any individual member or subgroup of members of the Markush group.

What is claimed is:

1. A complex of formula (I) of a bisphosphonate compound of formula (II), the complex adapted to target a bone,

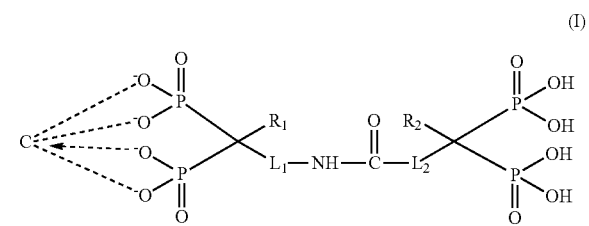

wherein, in formula (I), C represents a carrier to which the bisphosphonate compound of formula (II) is bound thereto, and wherein in formula (II), $R_1$ and $R_2$ are each independently selected from the group consisting of hydrogen, halogen, hydroxyl, $C_1$-$C_{10}$ alkyl, $C_2$-$C_6$ alkenyl, $C_2$-$C_6$ alkynyl, $C_1$-$C_6$ acyl, optionally substituted $C_{3-8}$ cycloalkyl, and $C_{3-8}$ cycloalkenyl; and $L_1$ and $L_2$ are each a linker having a main chain comprising 0 to 20 main chain atoms.

2. The complex of claim 1, wherein each of $L_1$ and $L_2$ is independently selected from the group consisting of $C_1$-$C_{20}$ alkyl, $C_0$-$C_6$ alkenyl, $C_0$-$C_6$ alkynyl, $C_0$-$C_6$ acyl, aryl, heteroaryl, $C_{3-8}$ cycloalkyl, and $C_{3-8}$ cycloalkenyl.

3. The complex of claim 1, wherein $L_1$ and $L_2$ are each independently selected from the group consisting of $C_1$-$C_{15}$ alkyl, aryl, and heteroaryl.

4. The complex of claim 3, wherein the $C_1$-$C_{15}$ alkyl is one of methyl, ethyl, propyl, butyl, pentyl, hexyl, heptyl, octyl, nonyl, decyl, undecyl, dodecyl, tridecyl, tetradecyl and pentadecyl.

5. The complex of claim 3, wherein the aryl is N—($C_1$-$C_6$alkyl)amino substituted aryl or N,N—($C_1$-$C_6$alkyl)amino aryl.

6. The complex of claim 5, wherein the N—($C_1$-$C_6$alkyl) amino substituted aryl is one of N-methylamino benzene or N-ethylamino benzene.

7. The complex of claim 5, wherein the N,N—($C_1$-$C_6$alkyl) amino aryl is one of N,N-diethylbenzene amine or N,N-dimethylamino benzene.

8. The complex of claim 2, wherein the heteroaryl is a $C_3$-$C_8$ heterocycle comprising at least one of nitrogen, oxygen or sulphur.

9. The complex of claim 8, wherein the heterocycle is 3-ethylpyridine or 1-ethylimidazole.

10. The complex of claim 1, wherein $R_1$ and $R_2$ are each independently hydrogen, hydroxyl or $C_1$-$C_6$ alkyl.

11. The complex of claim 1, wherein the complex is

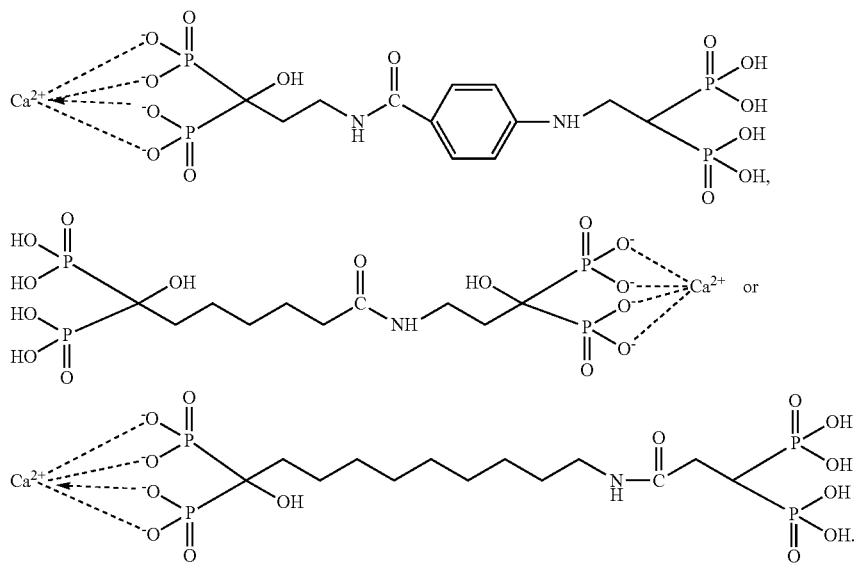

12. The complex of claim 1, wherein the carrier is selected from the group consisting of hydroxyapatite ($Ca_{10}(PO_4)_6(OH)_2$), calcium sulphate, hydroxyapatite composites of calcium sulphate and hydroxyapatite, hydroxyapatite composites of plaster of Paris, chitosan and hydroxyapatite, $\beta$-$Ca_3PO_4$, tricalcium phosphate, mono or biphasic calcium phosphate, calcium deficient apatite ($Ca_{10-x}(PO_4)_{6-x}(HPO_4)_x(OH)_{2-x}$), a polymeric carrier coated with calcium phosphate and combinations thereof.

13. The complex of claim 1, wherein the carrier is coated with hydroxyapatite or calcium phosphate.

14. The complex of claim 1, further comprising an additional medicament or drug.

15. The complex of claim 14, wherein the drug is an antibiotic, an antifungal, a peptide, a protein, a polymer, a nucleic acid molecule, or combinations thereof.

16. The complex of claim 1, further comprising a radioactive element.

17. The complex of claim 16, wherein the radioactive element is one selected from the group consisting of $^{99m}Tc$, $^{153}Sm$, $^{131}I$, $^{123}I$, $^{186}Re$ and $^{211}At$.

18. A pharmaceutical composition comprising a complex of formula (I) of a bisphosphonate compound of formula (II), the complex adapted to target a bone, (II)

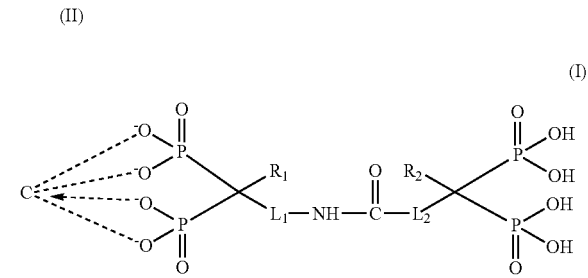

(I)

wherein,
in formula (I), C represents a carrier to which the bisphosphonate compound of formula (II) is bound thereto,
and wherein in formula (II),
$R_1$ and $R_2$ are each independently selected from the group consisting of hydrogen, halogen, hydroxyl, $C_1$-$C_{10}$ alkyl, $C_2$-$C_6$ alkenyl, $C_2$-$C_6$ alkynyl, $C_1$-$C_6$ acyl, $C_{3-8}$cycloalkyl, and $C_{3-8}$cycloalkenyl; and
$L_1$ and $L_2$ are each a linker having a main chain comprising 0 to 20 main chain atoms;
and a pharmaceutically acceptable carrier or excipient.

19. The pharmaceutical composition of claim 18, further comprising an additional medicament or drug.

20. A method for the treatment or of a bone-related disease or disorder, comprising administering a pharmaceutically active amount of a complex of formula (I) of a bisphosphonate compound of formula (II), the complex adapted to target a bone, (II)

(I)

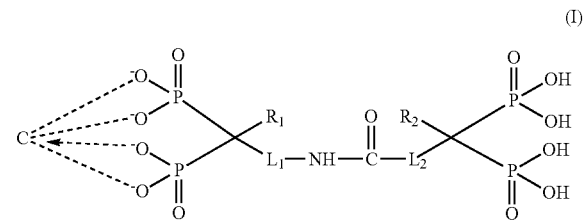

wherein,
in formula (I), C represents a carrier to which the bisphosphonate compound of formula (II) is bound thereto,
and wherein in formula (II),
$R_1$ and $R_2$ are each independently selected from the group consisting of hydrogen, halogen, hydroxyl, optionally substituted $C_1$-$C_{10}$ alkyl, optionally substituted $C_2$-$C_6$ alkenyl, optionally substituted $C_2$-$C_6$ alkynyl, optionally substituted $C_1$-$C_6$ acyl, optionally substituted $C_{3-8}$ cycloalkyl, and optionally substituted $C_{3-8}$ cycloalkenyl; and
$L_1$ and $L_2$ are each a linker having a main chain comprising 0 to 20 main chain atoms;
to a subject in need thereof.

21. The method of claim 20, wherein the subject is a mammal, preferably a human.

22. The method of claim 20, wherein the bone-related disease or disorder is one selected from the group consisting of osteoporosis, osteomyelitis, osteitis deformans ("Paget's disease of bone"), bone metastasis, multiple myeloma, primary hyperparathyroidism and osteogenesis imperfecta.

23. A complex of formula (I) of a bisphosphonate compound of formula (II), the complex adapted to target a bone, (II)

(I)

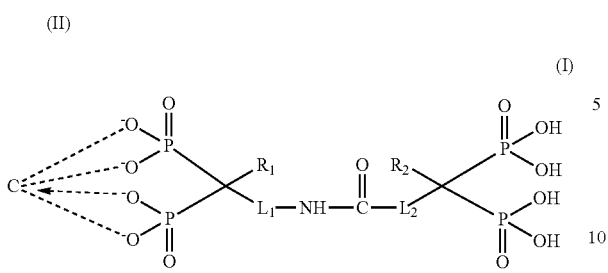

wherein,
in formula (I), C represents a carrier to which the bisphosphonate compound of formula (II) is bound thereto, and wherein in formula (II),
$R_1$ and $R_2$ are each independently selected from the group consisting of hydrogen, halogen, hydroxyl, $C_1$-$C_{10}$ alkyl, $C_2$-$C_6$ alkenyl, $C_2$-$C_6$ alkynyl, $C_1$-$C_6$ acyl, $C_{3-8}$ cycloalkyl, and $C_{3-8}$ cycloalkenyl; and
$L_1$ and $L_2$ are each a linker having a main chain comprising 0 to 20 main chain atoms, for use in the treatment or prevention of a bone-related disease or disorder.

24. A method of preparing the complex of formula (I), the method comprising reacting a compound of formula (IIa)

(IIa)

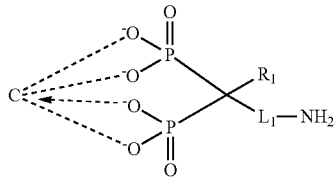

with a compound of formula (III), (III)

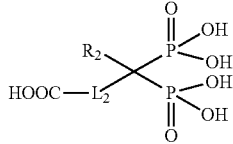

under conditions to form the complex of formula (I).

25. The method of claim 24, wherein the compound of formula (III) is formed by reacting a compound of formula (IV)

(IV)

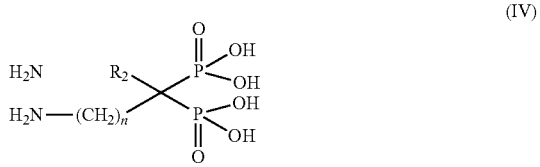

with a compound of formula (V), $$X\text{---}(CH_2)_n\text{---}COOH \qquad (V)$$

under conditions to form the compound of formula (III), wherein X is Br or F and n is an integer from 2 to 8.

26. A compound of formula (II)

(II)

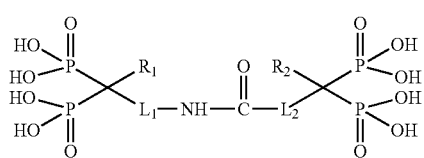

wherein
$R_1$ and $R_2$ are each independently selected from the group consisting of hydrogen, halogen, hydroxyl, $C_1$-$C_{10}$ alkyl, $C_2$-$C_6$ alkenyl, $C_2$-$C_6$ alkynyl, $C_1$-$C_6$ acyl, $C_{3-8}$ cycloalkyl, and $C_{3-8}$ cycloalkenyl; and
$L_1$ and $L_2$ are each a linker having a main chain comprising 0 to 20 main chain atoms, wherein each of $L_1$ and $L_2$ is independently selected from the group consisting of $C_1$-$C_{20}$ alkyl, $C_0$-$C_6$ alkenyl, optionally substituted $C_0$-$C_6$ alkynyl, $C_0$-$C_6$ acyl, aryl, heteroaryl, $C_{3-8}$ cycloalkyl, and $C_{3-8}$ cycloalkenyl.

* * * * *

UNITED STATES PATENT AND TRADEMARK OFFICE
CERTIFICATE OF CORRECTION

| | | |
|---|---|---|
| PATENT NO. | : 8,933,058 B2 | Page 1 of 1 |
| APPLICATION NO. | : 13/375713 | |
| DATED | : January 13, 2015 | |
| INVENTOR(S) | : Venkatraman et al. | |

It is certified that error appears in the above-identified patent and that said Letters Patent is hereby corrected as shown below:

In the claims:

Column 22,
Lines 33 and 34, cancel "optionally substituted".

Column 24,
Line 29, "treatment or of a bone-related disease" should read --treatment of a bone-related disease--.

Column 26,
Line 39, cancel "optionally substituted".

Signed and Sealed this
Twenty-fifth Day of August, 2015

Michelle K. Lee
*Director of the United States Patent and Trademark Office*